United States Patent
Ku et al.

(10) Patent No.: US 11,235,018 B2
(45) Date of Patent: Feb. 1, 2022

(54) COMPOSITION FOR PREVENTING OR TREATING CANCER

(71) Applicant: OKCHUNDANG CO., LTD., Daegu (KR)

(72) Inventors: Sae Kwang Ku, Daegu (KR); Seong Min Ku, Busan (KR); Tae Hun Ku, Busan (KR); Chui Jong Jung, Ulsan (KR); Gyung Yun Beik, Daegu (KR); Jin Gi Shin, Gyeongsan-si (KR); Sang Soo Lee, Daegu (KR); Jeong Gyun Seo, Daegu (KR); Chil Surk Yoon, Uiwang-si (KR); Xian Li, Daegu (KR)

(73) Assignee: OKCHUNDANG CO., LTD., Daegu (KR)

( * ) Notice: Subject to any disclaimer, the term of this patent is extended or adjusted under 35 U.S.C. 154(b) by 348 days.

(21) Appl. No.: 16/249,501

(22) Filed: Jan. 16, 2019

(65) Prior Publication Data

US 2019/0358283 A1 Nov. 28, 2019

(30) Foreign Application Priority Data

May 25, 2018 (KR) .................. 10-2018-0059573

(51) Int. Cl.

| A61K 36/64 | (2006.01) |
|---|---|
| A61K 36/258 | (2006.01) |
| A61K 36/342 | (2006.01) |
| A61K 36/076 | (2006.01) |
| A61K 31/5377 | (2006.01) |
| A61P 35/00 | (2006.01) |
| A23L 33/105 | (2016.01) |
| A61K 35/644 | (2015.01) |

(52) U.S. Cl.
CPC ............ *A61K 36/64* (2013.01); *A23L 33/105* (2016.08); *A61K 31/5377* (2013.01); *A61K 35/644* (2013.01); *A61K 36/076* (2013.01); *A61K 36/258* (2013.01); *A61K 36/342* (2013.01); *A61P 35/00* (2018.01); *A23V 2002/00* (2013.01)

(58) Field of Classification Search
None
See application file for complete search history.

(56) References Cited

FOREIGN PATENT DOCUMENTS

| CN | 106511864 A | 3/2017 |
|---|---|---|
| KR | 10-2005-0114167 A | 12/2005 |
| KR | 10-1719790 B1 | 3/2017 |
| KR | 10-2017-0113246 A | 10/2017 |

OTHER PUBLICATIONS

Kim (J Pharmacopuncture. Jun. 2017; 20(2): 81-88).*
Ham et al., "Antimutagenic and Antitumor Effects of Adenophora trlphylla Extracts," Journal of the Korean Society of Food Science and Nutrition. 38(1):25-31 (2009) (English abstract provided).
Hyun et al., "Effects of Bojungikkitang (a Polyherbal Formula), on Gefitinib Pharmacokinetics in Rats," International Journal of Pharmacology. 11(6):604-10 (2015).
Lee et al., "The Immunological Activities of Kyungohkgo and Prescription of Modified Kyungohkgo," Kor J Herbology. 17(2):95-100 (2002) (English abstract provided).
Shin et al., "The Experimental Studies on the Immunomodulational Effects of Adenophorae Radix," Kor J Herbology. 15(1):31-43 (2000) (English abstract provided).
Song et al., "Combined Treatment with Epimedium koreanum Nakai Extract and Gefitinib Overcomes Drug Resistance Caused by T790M Mutation in Non-Small Cell Lung Cancer Cells," Nutrition and Cancer. 66(4):682-89 (2014).
Office Action for Korean Application No. 2018-0059573 dated Jan. 29, 2019 (3 pages).

* cited by examiner

*Primary Examiner* — Susan Hoffman
(74) *Attorney, Agent, or Firm* — Clark & Elbing LLP; Susan M. Michaud

(57) ABSTRACT

The present invention provides a pharmaceutical composition for preventing or treating cancer, a food composition for enhancing immune functions, and a pharmaceutical composition for preventing or treating cachexia. The composition of the present invention provides effects of further inhibiting the growth of tumors, increasing immunological activity, and suppressing cachexia caused by tumors. In addition, the composition of the present invention can obtain a synergistic effect when co-administered with an existing anticancer drug.

3 Claims, 19 Drawing Sheets

COMPOSITION FOR PREVENTING OR TREATING CANCER

TECHNICAL FIELD

The present invention relates to a composition for preventing or treating cancer.

BACKGROUND ART

Gefitinib is a typical epidermal growth factor receptor (EGFR) inhibitor anti-cancer drug, which is frequently used as a medicine for various malignant tumors including breast cancer and lung cancer. It is known that gefitinib inhibits EGFR tyrosine kinase domains, and has very low toxicity, as a target-directed anticancer drug, compared with an existing cytotoxic anticancer drug. However, gefitinib causes a variety of undesired side effects, such as skin rash, diarrhea, nausea, vomiting, lack of appetite, gastritis, dehydration, nail pericarditis, hepatotoxicity, helplessness, conjunctivitis, blepharitis, interstitial lung disease, corneal erosion, and eyelash dropouts, and hypersensitivity responses of gefitinib per se or compositional components thereof, resulting in liver toxicity due to an increase in lipid peroxidation by the metabolome formed in the liver and the resultant damage to the antioxidative defense system. Recently, the emergency of resistant malignant tumor cells by EGFR mutation or the like has been a problem.

Therefore, there is a need for a new combination of co-administration that has the synergistic effect of chemotherapy while solving the toxicity and tolerance problems of gefitinib caused by co-administration of a natural material and a drug including various antioxidants.

PRIOR ART DOCUMENTS

Patent Documents (Patent Document 1) Korean Patent No. 10-1719790
(Patent Document 2) Korean Patent Publication No. 2017-0113246

Non-Patent Documents (Non-Patent Document 1) Hyun D S et al., Effects of Bojungikkitang (a Polyherbal Formula), on Gefitinib Pharmacokinetics in Rats. International Journal of Pharmacology 2015; 11(6):604-10
(Non-Patent Document 2) Song J et al., Combined treatment with Epimedium koreanum Nakai extract and gefitinib overcomes drug resistance caused by T790M mutation in non-small cell lung cancer cells. Nutrition and Cancer 2014; 66(4):682-9

DETAILED DESCRIPTION OF THE INVENTION

Technical Problem

The present inventors endeavored to develop a natural material showing a synergistic effect when co-administered with an existing anticancer drug. As a result, the present inventors established that the co-administration of a complex natural material comprising *Panax ginseng, Adenophorae triphylla, Wolfiporia extensa, Rehmannia glutinosa*, and mel as active ingredients with gefitinib as a medicine for various malignant tumors showed effects of further inhibiting the growth of tumors, increasing immunoreactivity, and suppressing cachexia caused by tumors, and therefore, completed the present invention.

Therefore, an aspect of the present invention is to provide a pharmaceutical composition for preventing or treating cancer.

Another aspect of the present invention is to provide a food composition for enhancing immune functions.

Still another aspect of the present invention is to provide a pharmaceutical composition for preventing or treating cachexia.

Still another aspect of the present invention is to provide a method for treatment of cancer.

Still another aspect of the present invention is to provide a method for enhancement of immune functions.

Still another aspect of the present invention is to provide a method for treatment of cachexia.

Technical Solution

In accordance with an aspect of the present invention, there is provided a pharmaceutical composition for preventing or treating cancer, the pharmaceutical composition comprising, as active ingredients, *Panax ginseng, Adenophorae triphylla, Wolfiporia extensa, Rehmannia glutinosa*, and mel.

The present inventors endeavored to develop a natural material showing a synergistic effect when co-administered with an existing anticancer drug. As a result, the present inventors established that the co-administration of a complex natural material comprising *Panax ginseng, Adenophorae triphylla, Wolfiporia extensa, Rehmannia glutinosa*, and mel as active ingredients with gefitinib as a medicine for various malignant tumors showed effects of further inhibiting the growth of tumors, increasing immunoreactivity, and suppressing cachexia caused by tumors.

*Panax ginseng* is a perennial herbaceous species, belonging to the family Araliaceae, about 60 cm in height, one new stem growing straightly each year, one flower stalk connecting from one end of the stem, and 3 to 6 verticillate petioles. Leaves have long petioles, and a leaf blade being divided into 3-5, forming palmately compound leaves. Hairs are on leaf veins on a front surface of the leaf. In summer, a thin flower stalk comes out, and 4-40 small flowers having a light yellowish color come out from the tip of the flower stalk, hung in the umbel inflorescence. The flowers have five leaves and stamens and one pistil, with an inferior ovary. The fruit thereof is drupe, has an elliptic shape, and turns into bright red when being ripe. Herein, *Panax ginseng* refers to roots thereof.

*Adenophorae triphylla* is a perennial herbaceous species, belonging to the family Campanulaceae. The stems are 50-100 cm in height straightly, and produce a white liquid when broken. Leaves have a long ellipse, 4-5 leaves are verticillate, with hairs on the stems and leaves. Several purplish flowers are versatile at the tip of the stem in July to October. The corolla has a bell shape and is 12-22 mm long. A style is divided into three, and is slightly longer than the corolla, and five stamens are dropped from the flower body. The stamen pole has a wide bottom and many hairs.

*Wolfiporia extensa* is a fungus in the family Polyporaceae, and includes Basidiomycota. The sclerotia are formed in pine roots in 10-30 cm underground, and are difformis. The surface is blackish reddish brown with creases, and the inside is white or red.

*Rehmannia glutinosa* is a perennial herbaceous species, belonging to the family Orobanchaceae, about 30 cm in height. Leaves with an ellipse shape come out from roots, and purple-red flowers come out in June and July. Herein, *Rehmannia glutinosa* refers to roots thereof.

Mel refers to sugar (honey) that is sucked and collected from flower nectarines by honey bees, e.g., *Apis cerana* or *Apis mellifera*.

The composition comprising, as active ingredients, *Panax ginseng, Adenophorae triphylla, Wolfiporia extensa, Rehmannia glutinosa*, and mel of the present invention is a composition for preventing or treating cancer.

As used herein, the term "cancer" refers to a disease in which the cell cycle is not normally regulated, resulting in continuous cell division. The cancer is synonymous with "malignant tumor" or "malignant neoplasm".

In an embodiment of the present invention, the cancer is selected from the group consisting of lung cancer, breast cancer, cervical cancer, pancreatic cancer, non-small cell lung cancer, liver cancer, colon cancer, bone cancer, skin cancer, head cancer, neck cancer, skin melanoma, intraocular melanoma, uterine cancer, ovarian cancer, rectal cancer, brain tumor, bladder cancer, blood cancer, gastric cancer, perianal cancer, fallopian tube carcinoma, endometrial carcinoma, vaginal cancer, vulvar carcinoma, Hodgkin's disease, esophageal cancer, small intestine cancer, endocrine gland cancer, thyroid cancer, parathyroid cancer, adrenal gland cancer, soft tissue sarcoma, urethral cancer, penis cancer, prostate cancer, bladder cancer, renal cancer, ureteral cancer, renal cell carcinoma, renal pelvis carcinoma, central nervous system (CNS) tumor, primary CNS lymphoma, spinal cord tumor, brainstem glioma, or pituitary adenoma, but is not limited thereto.

According to another embodiment of the present invention, the cancer is lung cancer or breast cancer.

As used herein, the term "prevention" refers to all actions that can inhibit cancer or delay the development of cancer through administration of the composition of the present invention.

As used herein, the term "treatment" refers to the inhibition of cancer development, amelioration of cancer, and removal of cancer.

The pharmaceutical composition for preventing or treating cancer of the present invention comprises, as active ingredients, *Panax ginseng, Adenophorae triphylla, Wolfiporia extensa, Rehmannia glutinosa*, and mel.

According to an embodiment of the present invention, the composition is prepared by mixing 4-5 wt % of *Panax ginseng*, 4-5 wt % of *Adenophorae triphylla*, 8-10 wt % of *Wolfiporia extensa*, 43-48 wt % of *Rehmannia glutinosa*, and 35-40 wt % of mel.

The *Panax ginseng, Adenophorae triphylla, Wolfiporia extensa, Rehmannia glutinosa*, and mel included in the composition of the present invention may be pulverized bodies, a suspension of pulverized bodies, a juice, or an extract.

The pulverized bodies may be prepared by various procedures. For example, the *Panax ginseng, Adenophorae triphylla, Wolfiporia extensa*, or *Rehmannia glutinosa* is subjected to a processing procedure, such as vacuum distillation, freeze-drying, or spray drying, and then may be used as pulverized bodies in various states, such as a powdered state, a homogenized state, a sliced state, and a mashed state.

According to an embodiment of the present invention, the *Panax ginseng, Adenophorae triphylla*, and *Wolfiporia extensa* are in a powdered state or a homogenized state, after freeze-drying.

The suspension of pulverized bodies may be prepared by various solutions. For example, distilled water or buffer (e.g., Tris buffer or HEPES buffer) may be used.

The juice may be prepared by various procedures. For example, the juice may be prepared by using gear type juicing using a compression effect, press type juicing, crush type juicing, or enzymatic degradation type juicing.

According to an embodiment of the present invention, the *Rehmannia glutinosa* is in a juice state.

According to another embodiment of the present invention, the *Rehmannia glutinosa* is a juice having a sugar content of 10-20 brix and a solid content of 10-20%.

According to other embodiment of the present invention, the composition comprises 4-5 wt % of *Panax ginseng* dried powder, 4-5 wt % of *Adenophorae triphylla* dried powder, 8-10 wt % of *Wolfiporia extensa* dried powder, 43-48 wt % of *Rehmannia glutinosa* juice extract, and 35-40 wt % of mel.

The extract may be prepared by various procedures. For example, the extract may be prepared by performing cold extraction, hot-water extraction, ultrasonic extraction, or reflux cooling extraction on a solvent crude extract obtained from the extraction with at least one solvent selected from the group consisting of water and $C_{1-4}$ alcohols.

The composition of the present invention may be prepared by aging a mixture of *Panax ginseng, Adenophorae triphylla, Wolfiporia extensa, Rehmannia glutinosa*, and mel.

According to an embodiment of the present invention, the aging may be carried out at a temperature of 80-100° C. for 10-100 hours.

The temperature may be 84-100° C., 88-100° C., 92-100° C., 94-100° C., 80-99° C., 80-98° C., 80-97° C., 84-99° C., 88-98° C., 92-97° C., or 94-97° C. The time may be 10-90 hours, 20-90 hours, 30-90 hours, 40-90 hours, 50-90 hours, 60-90 hours, 10-80 hours, 20-80 hours, 30-80 hours, 40-80 hours, 50-80 hours, 60-80 hours or 65-75 hours.

According to another embodiment of the present invention, the aging may be carried out once or more. The aging may be carried out twice or more by further including a step of performing cooling before secondary aging.

The cooling may be carried out at a temperature of 0-30° C. for 10-100 hours.

The present invention may further comprise an existing anticancer drug showing a synergistic effect in cancer therapy.

According to an embodiment of the present invention, the pharmaceutical composition for preventing or treating cancer of the present invention further comprises gefitinib.

As used herein, the term "gefitinib" refers to N-(3-chloro-4-fluorophenyl)-7-methoxy-6-(3-morpholinopropoxy)quinazolin-4-amine of chemical formula 1 below, which selectively inhibits epidermal growth factor receptor (EGFR) tyrosine kinase activity to inhibit the phosphorylation of EGFR, thereby blocking signaling from EFGR to inhibit the proliferation of cancer cells.

[Chemical formula 1]

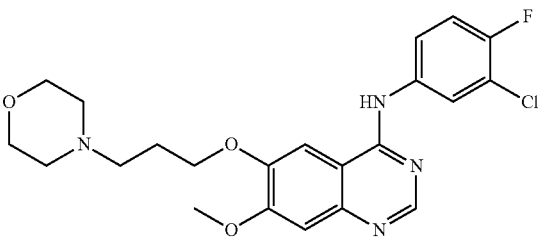

The co-administration of the composition of the present invention and gefitinib can show a synergistic effect compared with the administration of composition and gefitinib alone.

The pharmaceutical composition of the present invention may be used as a pharmaceutical composition comprising a pharmaceutically effective amount of a complex of *Panax ginseng, Adenophorae triphylla, Wolfiporia extensa, Rehmannia glutinosa*, and mel and/or a pharmaceutically acceptable carrier.

As used herein, the term "pharmaceutically effective amount" refers to the amount sufficient to attain the efficacy or activity of the complex.

The pharmaceutically acceptable carrier contained in the pharmaceutical composition of the present invention is usually used at the time of formulating, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The pharmaceutical composition of the present invention may further contain a lubricant, a humectant, a sweetener, a flavoring agent, an emulsifier, a suspending agent, and a preservative.

The pharmaceutical composition of the present invention may be administered orally or parenterally, and for example, intravenous administration, subcutaneous administration, intramuscular administration, intraperitoneal administration, topical administration, intranasal administration, intrapulmonary administration, rectal administration, intrathecal administration, ocular administration, skin administration, and transdermal administration may be employed.

An adequate dose of the pharmaceutical composition of the present invention varies depending on factors, such as the formulating method, manner of administration, patient's age, body weight, or gender, severity of disease, food, time of administration, route of administration, excretion rate, and response sensitivity, and an ordinarily skilled practitioner can easily judge and prescribe the dose effective for the desired treatment or prevention. According to a preferable embodiment of the present invention, the daily dose of the pharmaceutical composition of the present invention may be 0.0001-1000 mg/kg.

The pharmaceutical composition of the present invention may be formulated using a pharmaceutically acceptable carrier and/or excipient according to the method that is easily conducted by a person having ordinary skills in the art to which the present invention pertains, and the composition of the present invention may be prepared into a unit dosage form or may be inserted into a multi-dose container. Here, the dosage form may be a solution in a form of an oily or aqueous medium, a suspension, an emulsion, an extract, a powder, granules, a tablet, a capsule, or a gel (e.g., a hydrogel), and may further include a dispersing agent or a stabilizer.

According to another aspect of the present invention, the present invention provides a food composition comprising *Panax ginseng, Adenophorae triphylla, Wolfiporia extensa, Rehmannia glutinosa*, and mel as active ingredients for enhancing immune functions.

As used herein, the term "immune function" refers to a mechanism in which exogenous and endogenous antigens are physiologically recognized and excluded and homeostasis is maintained in human and animal bodies. The initial recognition of the antigens is mainly carried out by macrophages, and in this procedure, cytokines mediating immune responses are produced.

According to an embodiment of the present invention, the food composition for enhancing immune functions of the present invention increases the production of serum IFN-γ and splenic TNF-α.

Interleukin (IL) is a substance that plays an important role in the defense of the human body by acting on several stages for immune responses to regulate the immune responses.

According to an embodiment, the food composition for enhancing immune functions of the present invention increases the production of splenic IL-1β and IL-10.

The food composition for enhancing immune functions of the present invention can increase immune functions of a cancer patient.

According to an embodiment of the present invention, the composition of the present invention further comprises gefitinib.

The co-administration of the composition of the present invention and gefitinib can show a synergistic effect compared with the administration of the composition and gefitinib alone.

The composition of the present invention, when prepared as a food composition, comprises, in addition to *Panax ginseng, Adenophorae triphylla, Wolfiporia extensa, Rehmannia glutinosa*, and mel as active ingredients, the ingredients that are normally added at the time of food manufacturing, for example, proteins, carbohydrates, fats, nutrients, seasonings, and flavoring agents. Examples of the foregoing carbohydrate may include ordinary sugars (monosaccharides, such as glucose and fructose; disaccharides, such as maltose, sucrose and oligosaccharides; and polysaccharides, such as dextrin and cyclodextrin) and sugar alcohols, such as xylitol, sorbitol, and erythritol. Examples of the flavoring agent may include natural flavoring agents (thaumatin, and stevia extract (e.g., rebaudioside A, glycyrrhizin, etc.)) and synthetic flavoring agents (saccharin, aspartame, etc.). For example, the food composition of the present invention, when is prepared as a drink, may further contain, in addition to *Panax ginseng, Adenophorae triphylla, Wolfiporia extensa, Rehmannia glutinosa*, and mel, citric acid, liquefied fructose, sugar, glucose, acetic acid, malic acid, fruit juice, an *Eucommia ulmoides* extract, a jujube extract, and a licorice extract.

The food composition for enhancing immune functions of the present invention can be prepared into a health functional food composition.

The health functional food for enhancing immune functions comprises the ingredients that are ordinarily added at the time of food manufacturing, for example, proteins, carbohydrates, fats, nutrients, and seasonings. For example, the composition, which prepared as a drink, may contain, as an active ingredient, a hydrangea tea extract and, as an additional ingredient, a flavoring agent or natural carbohydrate. Examples of the natural carbohydrate include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). Natural flavoring agents (e.g., thaumatin, stevia extract, etc.) and synthetic flavoring agents (e.g., saccharin, aspartame, etc.) may be used as flavoring agents.

According to still another aspect of the present invention, the present invention provides a pharmaceutical composition for preventing or treating cachexia, the pharmaceutical composition comprising, as active ingredients, *Panax ginseng*, *Adenophorae triphylla*, *Wolfiporia extensa*, *Rehmannia glutinosa*, and mel.

As used herein, the term "cachexia" refers to a systematic malnutrition condition in which, regardless of the supplement of carries, nutritionally irreversible loss of body mass occurs due to a chronic disease, such as tuberculosis, cancer, or diabetes.

According to an embodiment of the present invention, the cachexia is caused by cancer.

Since the pharmaceutical composition for preventing or treating cachexia of the present invention is the same as the pharmaceutical composition for preventing or treating cancer with respect to active ingredients, the overlapping descriptions therebetween are omitted to avoid excessive complication of the specification.

Still another aspect of the present invention provides a method for treatment of cancer comprising a step:

administering, to a subject, a composition comprising *Panax ginseng*, *Adenophorae triphylla*, *Wolfiporia extensa*, *Rehmannia glutinosa*, and mel.

According to an embodiment of the present invention, wherein the composition comprises 4-5 wt % of *Panax ginseng*, 4-5 wt % of *Adenophorae triphylla*, 8-10 wt % of *Wolfiporia extensa*, 43-48 wt % of *Rehmannia glutinosa*, and 35-40 wt % of mel.

According to another embodiment of the present invention, wherein the composition comprises 4-5 wt % of *Panax ginseng* dried powder, 4-5 wt % of *Adenophorae triphylla* dried powder, 8-10 wt % of *Wolfiporia extensa* dried powder, 43-48 wt % of *Rehmannia glutinosa* juice extract, and 35-40 wt % of mel.

According to an embodiment of the present invention, wherein the composition further comprises gefitinib.

According to another embodiment of the present invention, the method further comprises a step administering gefitinib to the subject. Gefitinib can be administered within 5 min after administering the composition comprising *Panax ginseng*, *Adenophorae triphylla*, *Wolfiporia extensa*, *Rehmannia glutinosa*, and mel.

Still another aspect of the present invention provides a method for enhancement of immune functions comprising a step:

administering, to a subject, a composition comprising *Panax ginseng*, *Adenophorae triphylla*, *Wolfiporia extensa*, *Rehmannia glutinosa*, and mel.

According to an embodiment of the present invention, wherein the composition further comprises gefitinib.

According to another embodiment of the present invention, the method further comprises a step administering gefitinib to the subject. Gefitinib can be administered within 5 min after administering the composition comprising *Panax ginseng*, *Adenophorae triphylla*, *Wolfiporia extensa*, *Rehmannia glutinosa*, and mel.

According to an embodiment of the present invention, wherein the method is for enhancement of immune functions in a cancer patient.

According to another embodiment of the present invention, wherein the method is for enhancement of immune response in the subject, wherein the immune response is indicated by activation of antigen presenting cells (macrophages, B cells and dendritic cells) or increase/production of immune cytokines.

The initial recognition of the antigens is mainly carried out by macrophages, and in this procedure, cytokines mediating immune responses are produced.

According to an embodiment of the present invention, the composition for enhancing immune functions of the present invention increases the production of serum IFN-γ and splenic TNF-α.

Interleukin (IL) is a substance that plays an important role in the defense of the human body by acting on several stages for immune responses to regulate the immune responses.

According to an embodiment, the composition for enhancing immune functions of the present invention increases the production of splenic IL-1β and IL-10.

Still another aspect of the present invention provides a method for treatment of cachexia comprising a step:

administering, to a subject, a composition comprising *Panax ginseng*, *Adenophorae triphylla*, *Wolfiporia extensa*, *Rehmannia glutinosa*, and mel.

According to an embodiment of the present invention, wherein the composition further comprises gefitinib.

According to another embodiment of the present invention, the method further comprises a step administering gefitinib to the subject. Gefitinib can be administered within 5 min after administering the composition comprising *Panax ginseng*, *Adenophorae triphylla*, *Wolfiporia extensa*, *Rehmannia glutinosa*, and mel.

Advantageous Effects

Features and advantages of the present invention are summarized as follows.

(a) The present invention provides a pharmaceutical composition for preventing or treating cancer, a food composition for enhancing immune functions, and a pharmaceutical composition for preventing or treating cachexia.

(b) The composition of the present invention provides effects of further inhibiting the growth of tumors, increasing immunological activity, and suppressing cachexia caused by tumors.

(c) The composition of the present invention can obtain a synergistic effect when co-administered with an existing anticancer drug.

BRIEF DESCRIPTION OF THE DRAWINGS

In FIGS. 10 to 15, A represents a NCI-H520 tumor cell xenografted and then sterile distilled water administered group, B represents a tumor cell xenografted and then gefitinib 120 mg/kg single composition administered group, C represents SKOG400: a tumor cell xenografted and then SKOG 400 mg/kg single administered group, D represents a tumor cell xenografted and then gefitinib 120 mg/kg and SKOG 400 mg/kg co-administered group, E represents a tumor cell xenografted and then gefitinib 120 mg/kg and SKOG 200 mg/kg co-administered group, F represents a tumor cell xenografted and then gefitinib 120 mg/kg and SKOG 100 mg/kg co-administered group.

FIG. 11 shows analysis images of intratumoral caspase immune response cells in tumor cell xenograft mice according to SKOG or gefitinib single administration and SKOG and gefitinib co-administration.

FIG. 12 shows analysis images of intratumoral PARP immune response cells in tumor cell xenograft mice according to SKOG or gefitinib single administration and SKOG and gefitinib co-administration.

FIG. 13 shows analysis images of intratumoral COX-2 immune response cells in tumor cell xenograft mice according to SKOG or gefitinib single administration and SKOG and gefitinib co-administration.

FIG. 14 shows analysis images of intratumoral iNOS immune response cells in tumor cell xenograft mice according to SKOG or gefitinib single administration and SKOG and gefitinib co-administration.

FIG. 15 shows analysis images of intratumoral TNF-α immune response cells in tumor cell xenograft mice according to SKOG or gefitinib single administration and SKOG and gefitinib co-administration.

In FIGS. 16 to 18, A represents a normal medium control group, B represents a NCI-H520 tumor cell xenografted and then sterile distilled water administered group, C represents a tumor cell xenografted and then gefitinib 120 mg/kg single composition administered group, D represents SKOG400: a tumor cell xenografted and then SKOG 400 mg/kg single administered group, E represents a tumor cell xenografted and then gefitinib 120 mg/kg and SKOG 400 mg/kg co-administered group, F represents a tumor cell xenografted and then gefitinib 120 mg/kg and SKOG 200 mg/kg co-administered group, G represents a tumor cell xenografted and then gefitinib 120 mg/kg and SKOG 100 mg/kg co-administered group.

FIG. 17 shows changes of cortex (CO), medullar (ME), and follicles (FO) in submandibular lymph nodes in tumor cell xenograft mice according to SKOG or gefitinib single administration and SKOG and gefitinib co-administration.

FIG. 18 shows images of periovarian fat in tumor cell xenograft mice according to SKOG or gefitinib single administration and SKOG and gefitinib co-administration.

MODE FOR CARRYING OUT THE INVENTION

Figure 1A:
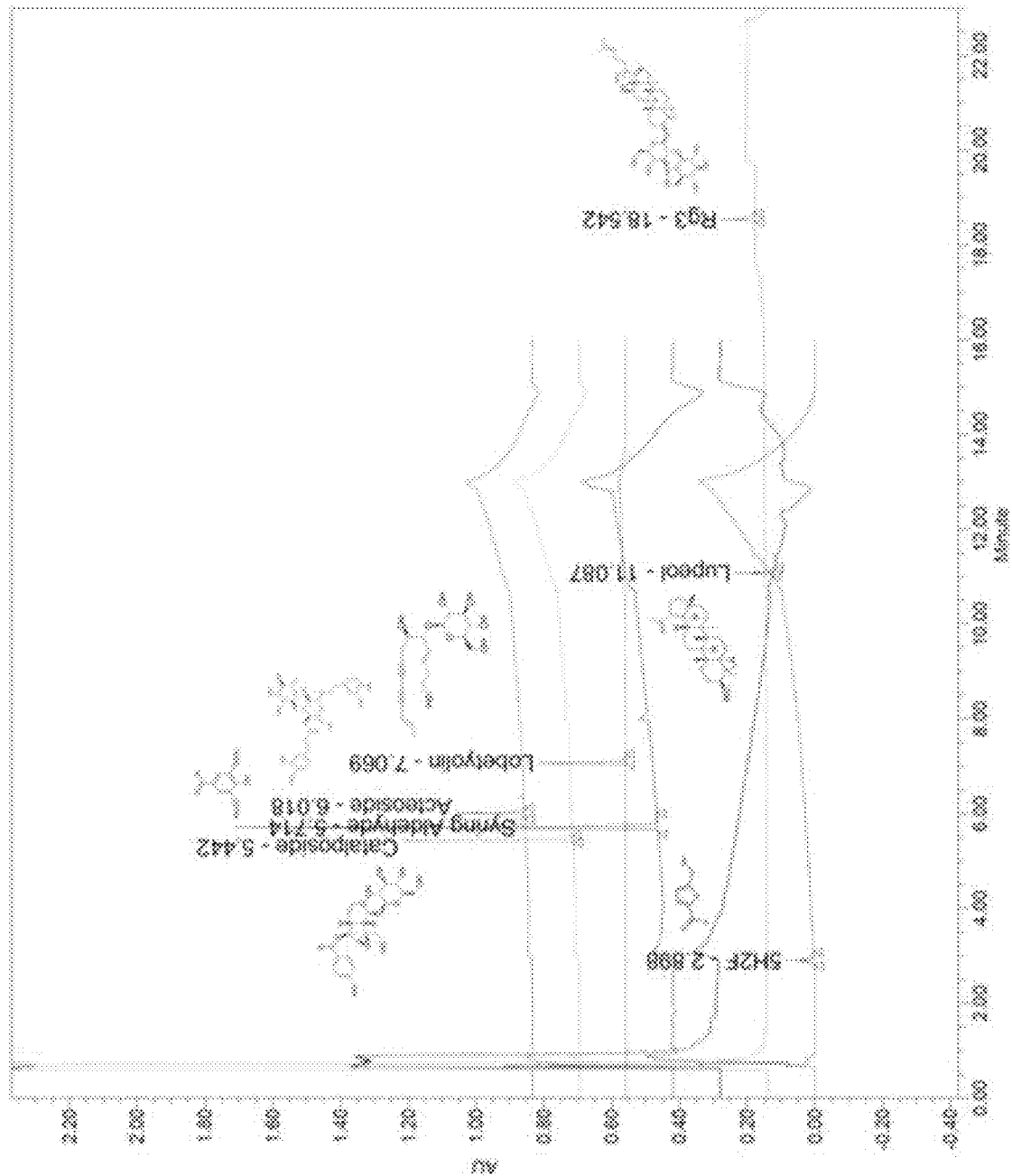
FIGS. 1*a* and 1*b* show ultra performance liquid chromatography (UPLC) analysis results of a standard solution and SKOG, respectively.

Hereinafter, the present invention will be described in detail with reference to examples. These examples are only for illustrating the present invention more specifically, and it would be obvious to those skilled in the art that the scope of the present invention is not limited by these examples.

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

Example 1: Preparation of Complex Natural Material (1) Materials

*Adenophor triphylla* Radix (AR, Andong, Gyeongsangbukdo, Korea), *Panax ginseng* (Geumsan, Chungcheongnamdo, Korea), *Poria cocos* Wolf/*Wolfiporia extensa* (Anhui, Chinese), *Rehmannia glutinosa* (Andong and Gunwi, Gyeongsangbukdo, Korea), and mel (Okcheon, Chungcheongbukdo, Korea) were used from Okcheon Dang Pharmaceutical Co., Ltd. (Yeongcheon, Korea). Some test materials were kept in Medical Research center for Globalization of Herbal Formulation, Daegu Haany University, Gyeongsan, Korea) (Code No. *Adenophora triphylla*—AR2016Ku01, KOG—KOG2016Ku01, SKOG—SKOG2016Ku01). AR were stored at 4° C. in a refrigerator until use.

(2) Preparation Method for SKOG

*Adenophor triphylla* Radix was washed to remove impurities, such as soil, followed by removal of moisture, and then dried at 90-120° C. for 5-8 hours by hot-air drying or other drying methods, to a final moisture content of 5% or less. The dried product was prepared into a powder having a particle size of 80 mesh or more by using a pulverizer, such as a pin mill, a ball mill, a rod mill, an air mill, or a jet mill. *Poria cocos* Wolf was washed to remove impurities, such as soil, followed by removal of moisture, and then the surface thereof was completely dried. *Panax ginseng* was washed against impurities, such as soil, to remove moisture, and then dried at 90-120° C. for 5-8 hours by hot-air drying or other drying methods, to a final moisture content of 5% or less. The dried *Poria cocos* Wolf and *Panax ginseng* were prepared into a powder having a particle size of 80 mesh or more by using a pulverizer, such as a pin mill, a ball mill, a rod mill, an air mill, or a jet mill. *Rehmannia glutinosa* was washed to remove impurities, such as soil, followed by removal of moisture, pulverized through a mechanical pulverizer, such as a blender, and then passed through a net or a filter with 70-mesh through a mechanical juicing device, such as a hydraulic presser to obtain a juice thereof. The juice needs to have a sugar content of 15-18 brix and a solid content of 13-16%, and needs to have a yield of 70% or more in the process of obtaining the juice through pulverization. Mel was processed to have a moisture content of 22-24% by heating at 80-85° C.

The thus obtained materials, 4-5 wt % of the *Panax ginseng* powder, 8-10 wt % of the *Poria cocos* Wolf powder, 4-5 wt % of the *Adenophora triphylla* powder, 35-40 wt % of mel, and 43-48 wt % of the *Rehmannia glutinosa* juice were mixed (table 1), followed by first aging at 94.5-96.5° C. for 72 hours, first cooling at 8-12° C. for 24 hours, second aging at 94.5-96.5° C. for 24 hours, and second cooling at room temperature for 72 hours, thereby preparing KOG.

TABLE 1

| Natural material | Scientic name | Production area | Amount (g) |
|---|---|---|---|
| Panax ginseng | Panax ginseng C. A. Meyer | Korea | 4,500 |

TABLE 1-continued

| Natural material | Scientic name | Production area | Amount (g) |
|---|---|---|---|
| Wolfiporia extensa | Poria cocos Wolf | China | 9,000 |
| Adenophor triphylla | Adenophora triphylla var. japonica Hara | Korea | 4,500 |
| Mel | — | Korea | 39,000 |
| Rehmannia glutinosa | Rehmannia glutinosa(Gaertner) Liboschitz ex Steudel | Korea | 47,000 |
| — | — | — | 104,000 |

Example 2: Analysis of Index Ingredients in SKOG (1) Instruments and Reagents

Waters ACQUITY™ ultra performance LC system (Waters Corporation, Milford, Mass., USA) equipped with Waters ACQUITY™ photodiode array detector (PDA; Waters Corporation, Milford, Mass., USA) was used as ultra performance liquid chromatography (UPLC). Waters ACQUITY™ BEH C18 column (1.7 µm, 2.1×100; Waters Corporation, Milford, Mass., USA) was used as an HPLC column, and Empower (Waters Corporation, Milford, Mass., USA) was used as software. An extractor used in sample extraction was the ultrasonicator model 8210R-DHT (Branson Ultrasonics, Danbury, Conn.). Reagents used for this experiment were methanol (HPLC grade, Junsei Chemical Co., Ltd., Tokyo, Japan), acetonitrile (HPLC grade, BAKER, Center Valley, Pa., USA), and water (Tertiary distilled water). The standard preparations used in the experiment were purchased from the Sigma-Aldrich (St. Louise, Mo., USA) or Extrasynthese (Genay Cedex, France).

(2) Preparation of Standard Solution

Lupeol, which is a substance contained in *Adenophorae triphylla*, was dissolved in dimethyl sulfoxide (DMSO) to prepare a standard stock solution with a concentration of 1 µg/ml. Lobetyolin and syring aldehyde, which are substances contained in *Adenophorae triphylla*, acteoside, catalposide, and 5-hydroxymethyl-2-furfural (5H2F), which are substances contained in *Rehmannia glutinosa*, ginsenosides Rg3 and Rg3, which are substances contained in *Panax ginseng*, were dissolved in methanol, respectively, to prepare standard stock solutions with a concentration of 1 µg/ml. Thereafter, an appropriate amount of each standard stock solution was taken, and diluted with methanol so as to contain 1, 5, and 10 g per ml of methanol, which was set as standard solutions. A standard curve determination coefficient ($R^2$) value was more than 0.999 of all standard substances.

(3) Preparation of Test Liquid for Quantitative Analysis

A test liquid for quantitative analysis was homogeneously mixed with the sample, which was weighed 1 g precisely, and 10 ml of 30% methanol was added thereto, followed by ultrasonic extraction for 1 hr. This resultant test liquid was filtered through a membrane filter with a pore diameter of 0.2 µm or less, and was picked out as a test liquid.

(4) Quantification of Sample

Waters ACQUITY™ ultra performance LC system (USA) was used as ultra performance liquid chromatography (UPLC). UPLC equipped with a photodiode array detector (PDA) and a bridged ethylene hydride (BEH) C18 column was used to analyze the index substances, and quantified by using Empower software. PDAA wavelength analysis was conducted at 280 nm for lupeol, acteoside, catalposide, and 5H2F, and 310 nm and 254 nm for lobetyolin and syring aldehyde, respectively. The temperature of the column was analyzed at the room temperature. A mobile phase was a mixed liquid of acetonitrile and water, containing 0.1% formic acid. The analysis was conducted under the conditions shown in table 2 below.

TABLE 2

| Time(min) | 0.1% FA/water(%) | 0.1% FA/acetonitrile(%) | Flow rate(ml/min) |
|---|---|---|---|
| 0 | 98 | 2 | 0.40 |
| 1.0 | 98 | 2 | 0.40 |
| 2.0 | 90 | 10 | 0.40 |
| 4.0 | 70 | 30 | 0.40 |
| 7.0 | 50 | 50 | 0.40 |
| 9.0 | 30 | 70 | 0.40 |
| 10.0 | 10 | 90 | 0.40 |
| 12.0 | 0 | 100 | 0.40 |
| 14.0 | 98 | 2 | 0.40 |
| 16.0 | 98 | 2 | 0.40 |

Rg3 was analyzed at 203 nm, and the mobile phase was a mixed liquid of acetonitrile and water. The analysis was conducted under the conditions shown in table 3 below.

TABLE 3

| Time(min) | water(%) | acetonitrile(%) | Flow rate(ml/min) |
|---|---|---|---|
| 0 | 85 | 15 | 0.40 |
| 1.0 | 85 | 15 | 0.40 |
| 14.0 | 70 | 30 | 0.40 |
| 15.0 | 68 | 32 | 0.40 |
| 16.0 | 60 | 40 | 0.40 |
| 17.0 | 45 | 55 | 0.40 |
| 19.0 | 45 | 55 | 0.40 |
| 21.0 | 10 | 90 | 0.40 |
| 22.0 | 10 | 90 | 0.40 |
| 23.0 | 85 | 15 | 0.40 |

The sample was injected with 2 µl, and a flow rate was 0.4 ml/min. As a result of analysis, qualitative checking was conducted by the retention time and quantitative analysis was conducted by the peak area method.

Figure 1B:
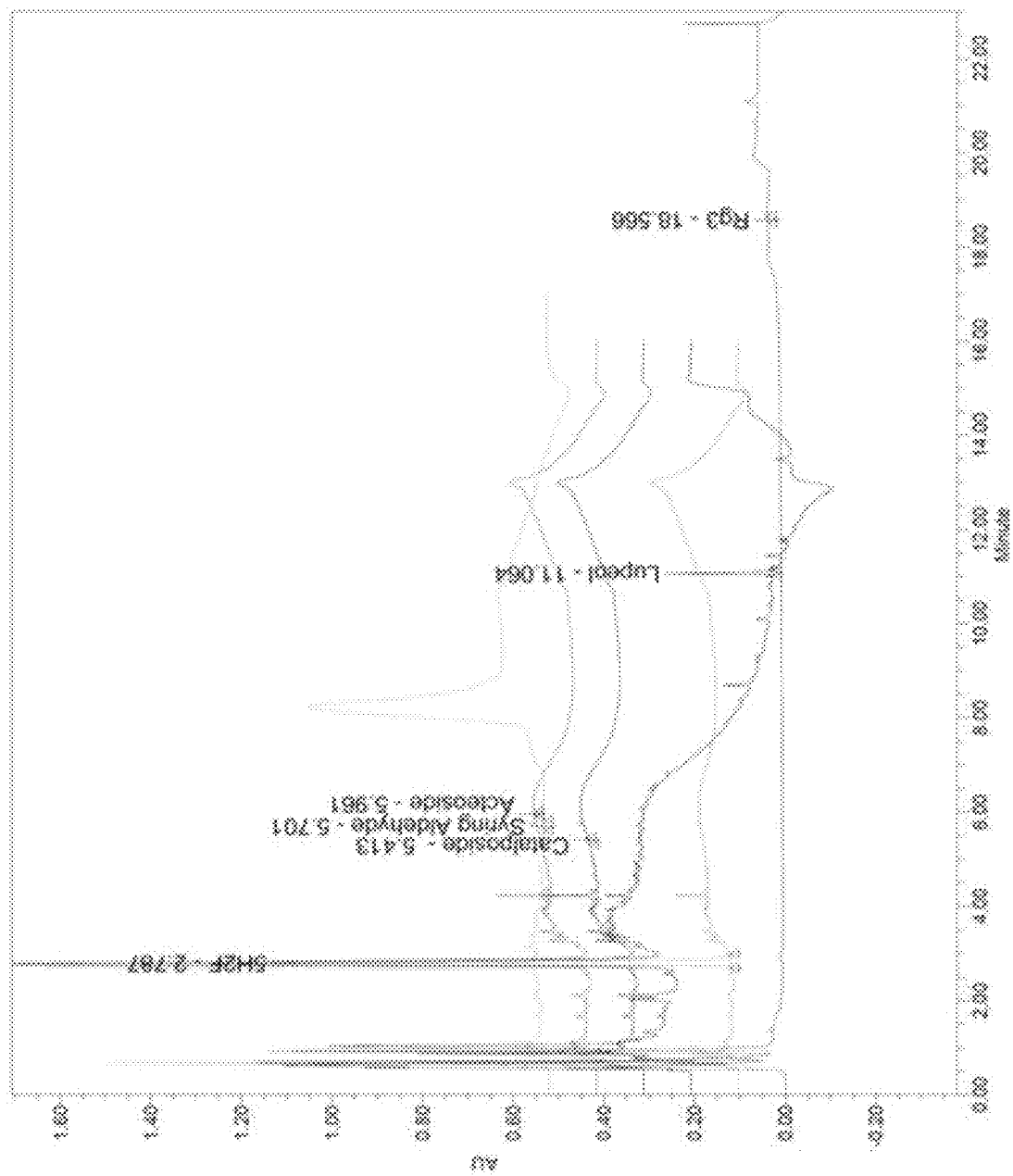

The results are shown in Table 4 and FIGS. 1a and 1b.

TABLE 4

| Ingredient | Concentration (mg/kg) |
|---|---|
| Lupeol | 224.52 ± 12.5 |
| Lobetyolin | — |
| Syring aldehyde | 0.14 ± 0.01 |
| 5H2F | 559.50 ± 1.70 |
| Acteoside | 0.31 ± 0.01 |
| Catalposide | 0.33 ± 0.01 |
| Rg3 | 4.42 ± 0.02 |

FIGS. 1a and 1b show UPLC analysis results of standard solutions and SKOG, respectively. As shown in Table 4 and FIGS. 1a and 1b, it was observed in the UPLC analysis results that SKOG contained lupeol, lobetyolin, and syring aldehyde, 5H2F, acteoside, catalposide, and Rg3 of 224.52±12.5, 0.14±0.01, 559.50±1.70, 0.31±0.01, 0.33±0.01, and 4.42±0.02 mg/kg, respectively.

Example 3: Anticancer Effect

(1) Materials

A dark brown viscous composition (SKOG) in which *Adenophorae triphylla, Panax ginseng, Wolfiporia extensa, Rehmannia glutinosa*, and mel were mixed was provided from Okchundang (Korea), and some test materials were kept in Medical Research center for Globalization of Herbal Formulation, Daegu Haany University, Gyeongsan, Korea) (Code No. SKOG2017Ku01). A pale yellow gefitinib powder was purchased from Suzhou Huihe Pharm Co., Ltd. (Suzhou, China; ANNEX IV).

NCI-H520 lung cancer cells (ATCC HTB-182) were incubated in RPMI 1640 media (Gibco BRL, Grand Island. N.Y., USA) supplemented with 10% fatal bovine serum (FBS; Gibco BRL, Grand Island. N.Y., USA), 100 U/ml penicillin (Sigma-Aldrich, St. Louise, Mo., USA), and 100 μg/ml streptomycin (Sigma-Aldrich, St. Louise, Mo., USA) at 37° C. 5% $CO_2$ condition (Model 311, Thermo Forma, Marietta, Ohio, USA). Generally, gefitinib is known to show $IC_{50}$ of about 0.1 μM on sensitive EGFR expressed tumor cell lines, but show $IC_{50}$ of 1 μM or more on resistant cell lines with EGFR mutation [Han et al., 2012]. The NCI-H520 used in the present test showed $IC_{50}$ of 4.56±1.46 μM (2.00±0.64 μg/ml) to gefitinib. From 15 days after the xenograft of NCI-H520 lung cancer cells ($2\times10^7$ cells/mouse), the composition in which *Adenophorae triphylla, Panax ginseng, Wolfiporia extensa, Rehmannia glutinosa*, and mel were mixed was suspended in sterile distilled water at concentrations of 40, 20, and 10 mg/ml, respectively, and then the mice, which had been orally administered with 120 mg/kg gefitinib were co-administered with respective suspensions at a dose of 10 ml/kg (400, 200, and 100 mg/kg) at an interval of within 5 min for 35 days once every day. Also, gefitinib was dissolved in sterile distilled water to a concentration of 12 mg/ml, and orally administered into the mice at a dose of 10 ml/kg (120 mg/kg). In addition, for the provision of stress due to the same administration and restrain, only the same volume of sterile distilled water was administered to each single administration group when the composition in which *Adenophorae triphylla, Panax ginseng, Wolfiporia extensa, Rehmannia glutinosa*, and mel were mixed or gefitinib was administered, and only sterile distilled water as a medium was administered to the normal and tumor transplant medium control groups twice at an interval of within 5 min.

(2) Cytotoxic Evaluation $IC_{50}$ at which SKOG (0, 0.01, 0.1, 0.5, 1, 5, 10, and 40 mg/kg) and gefitinib (0, 0.001, 0.01, 0.1, 1, 5, 10, and 50 μM) inhibited cell viability of NCI-H520 cells ($1\times10^4$ cell) by 50% was evaluated by using the MTT method.

Figure 2:
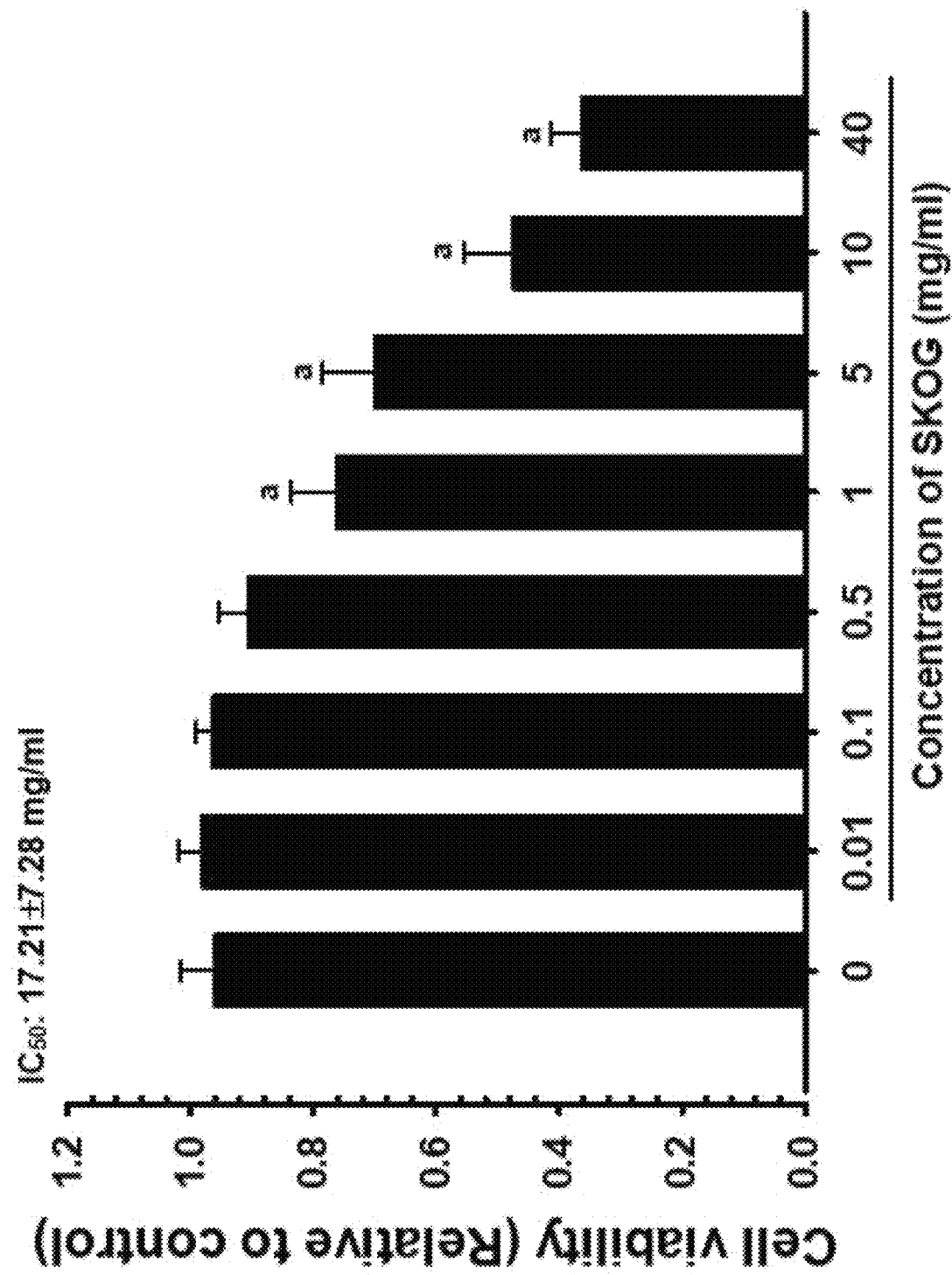
FIG. 2 shows cell viability results of NCI-H20 against SKOG 0.01 to 40 mg/ml treatment.

As a result, the cell viability of NCI-H520 cells was significantly reduced in from SKOG 1 mg/ml treated group, compared with the medium control group (1 mg/ml treated group) ($p<0.01$), and $IC_{50}$ was calculated as 17.21±7.28 mg/ml (FIG. 2). The cell viability of NCI-H520 cells showed changes of 2.10, 0.30, −5.72, −20.61, −27.03, −50.53, and −62.23% in the SKOG 0.01, 0.1, 0.5, 1, 5, 10. and 40 mg/ml treated groups, respectively, compared with the non-treated medium control group (0 mg/ml treated group).

Figure 3:
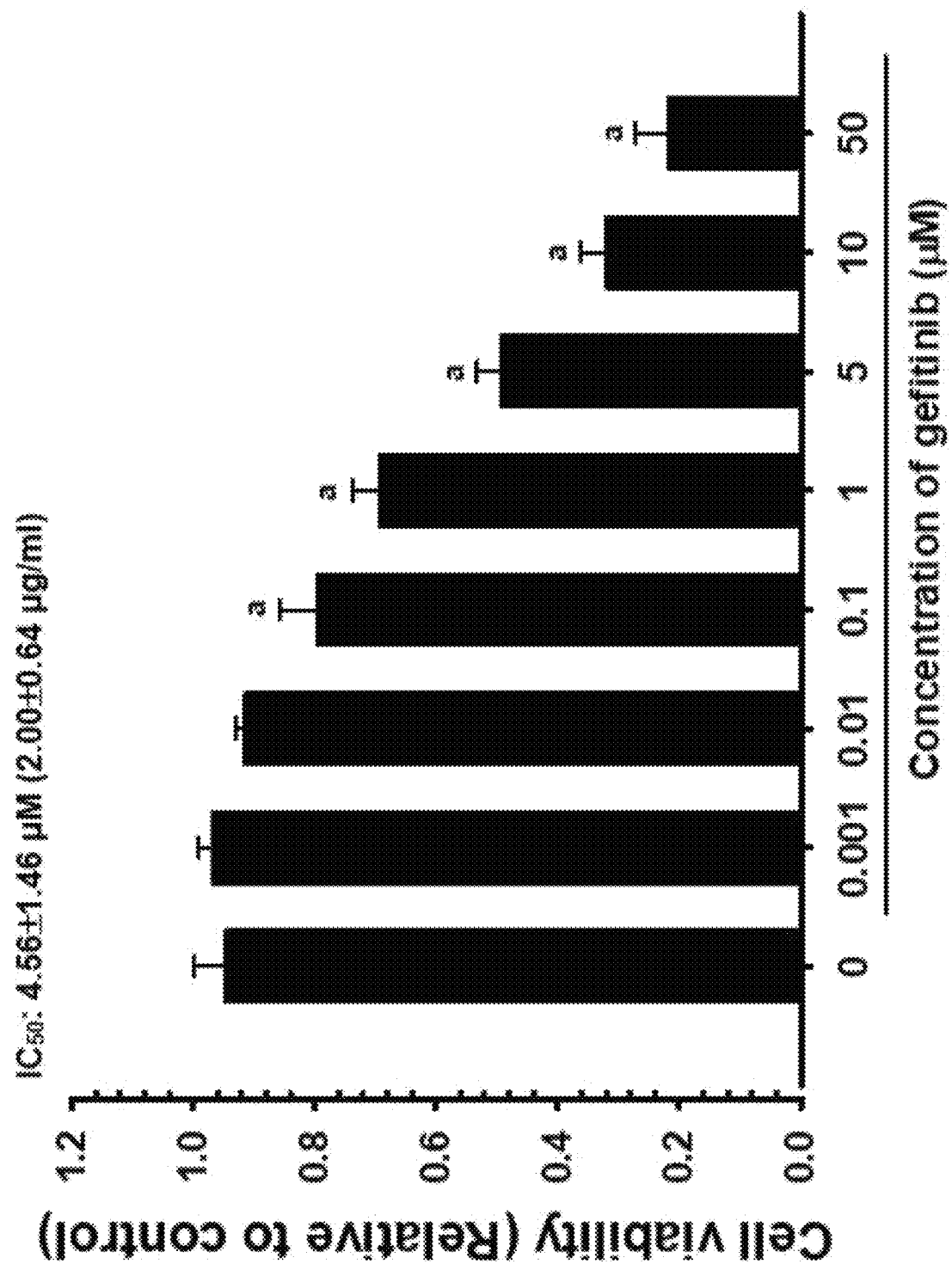
FIG. 3 shows cell viability results of NCI-H20 against gefitinib 0.001 to 50 mg/ml treatment.

In addition, the cell viability of NCI-H520 cells was significantly reduced in from gefitinib 0.1 μM treated group, compared with the medium control group (0 μM treated group) ($p<0.01$), and $IC_{50}$ was calculated as 4.56±1.46 μM (FIG. 3). The cell viability of NCI-H520 cells showed changes of 2.81, −3.53, −16.05, −26.95, −48.01, −66.29, and −76.96% in the gefitinib 0.001, 0.01, 0.1, 1, 5, 10, and 50 μM treated groups, respectively, compared with the non-treated medium control group (0 μM treated group).

(3) Animals

Figure 4:
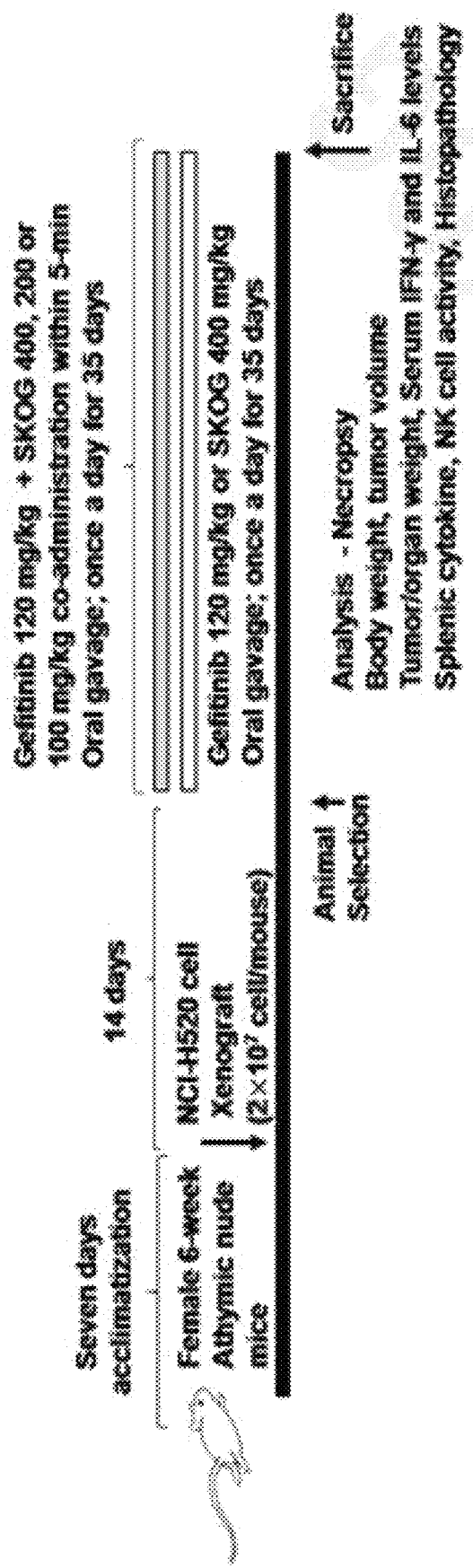
FIG. 4 shows a tumor cell subcutaneous transplantation and immunization schedule of experimental animals.

A total of 140 SPF/VAF Hsd:Athymic Nude-Foxn1nu mice (6-week age female. Harlan Lab., Udine Italy) [ANNEX I, II] were acclimatized for 7 days, and then animals with a predetermined weight were selected, xenografted with NCI-H520 cells ($2\times10^7$ cells/mouse) into the subcutaneous area of the right buttock. On day 14 after the xenograft of tumor cells, xenograft mice with a tumor volume of 500.14±125.31 $mm^3$ (314.87~771.33 $mm^3$) or more were again selected, and eight mice per group were used in the present test. A normal medium control group of separate eight mice was also prepared on the basis of the body weight (body weight: normal group—21.34±1.20 g, 19.80-23.20 g; tumor xenograft group—21.35±1.15 g, 19.40-23.60 g). The present animal experiment was conducted under the prior approval of the Institutional Animal Care and Use Committee in Daegu Haany University (Approval No. DHU2017-098, Sep. 25, 2017; ANNEX III) (FIG. 4).

<Group Classification (a Total of Seven Groups; Eight Animals Per Group)>

(1) Intact control: Normal medium control group (2) TB (tumor bearing) control: NCI-H520 tumor cell xenografted and then sterile distilled water administered group (3) G120: Tumor cell xenograft and then gefitinib 120 mg/kg alone-administered group (4) SKOG400: Tumor cell xenografted and then composition (*Adenophorae triphylla, Panax ginseng, Wolfiporia extensa, Rehmannia glutinosa*, and mel being mixed) 400 mg/kg single administered group (5) GSK400: Tumor cell xenografted and then gefitinib 120 mg/kg and composition (*Adenophorae triphylla, Panax ginseng, Wolfiporia extensa, Rehmannia glutinosa*, and mel being mixed) 400 mg/kg co-administered group (6) GSK200: Tumor cell xenografted and then gefitinib 120 mg/kg and composition (*Adenophorae triphylla, Panax ginseng, Wolfiporia extensa, Rehmannia glutinosa*, and mel being mixed) 200 mg/kg co-administered group (7) GSK100: Tumor cell xenografted and then gefitinib 120 mg/kg and composition (*Adenophorae triphylla, Panax ginseng, Wolfiporia extensa, Rehmannia glutinosa*, and mel being mixed) 100 mg/kg co-administered group

(4) Xenograft of Tumor Cells

NCI-H520 (American Type Culture Collection Center, Manassas, Va., USA) cells were subcultured and maintained in a 37° C. 5% $CO_2$ incubator using RPMI 1640 (Gibco, Grand Island, N.Y., USA) supplemented with 10% fetal bovine serum (FBS), and a tumor cell floating liquid was prepared to have $1.0\times10^8$ cell/ml. In addition, 0.2 mL ($2\times10^7$ cell/mouse) of NCI-H520 cell floating liquid was injected into the subcutaneous area of the right buttock to form solid tumor masses. In the present experiment, gefitinib or an experimental diet was orally administered from 21 days after the xenograft of NCI-H520 lung cancer cell lines (tumor volume: 500.14±125.31 $mm^3$, 314.87~771.33 $mm^3$).

(5) Changes in Body Weight and Weight Gain

Figure 5:
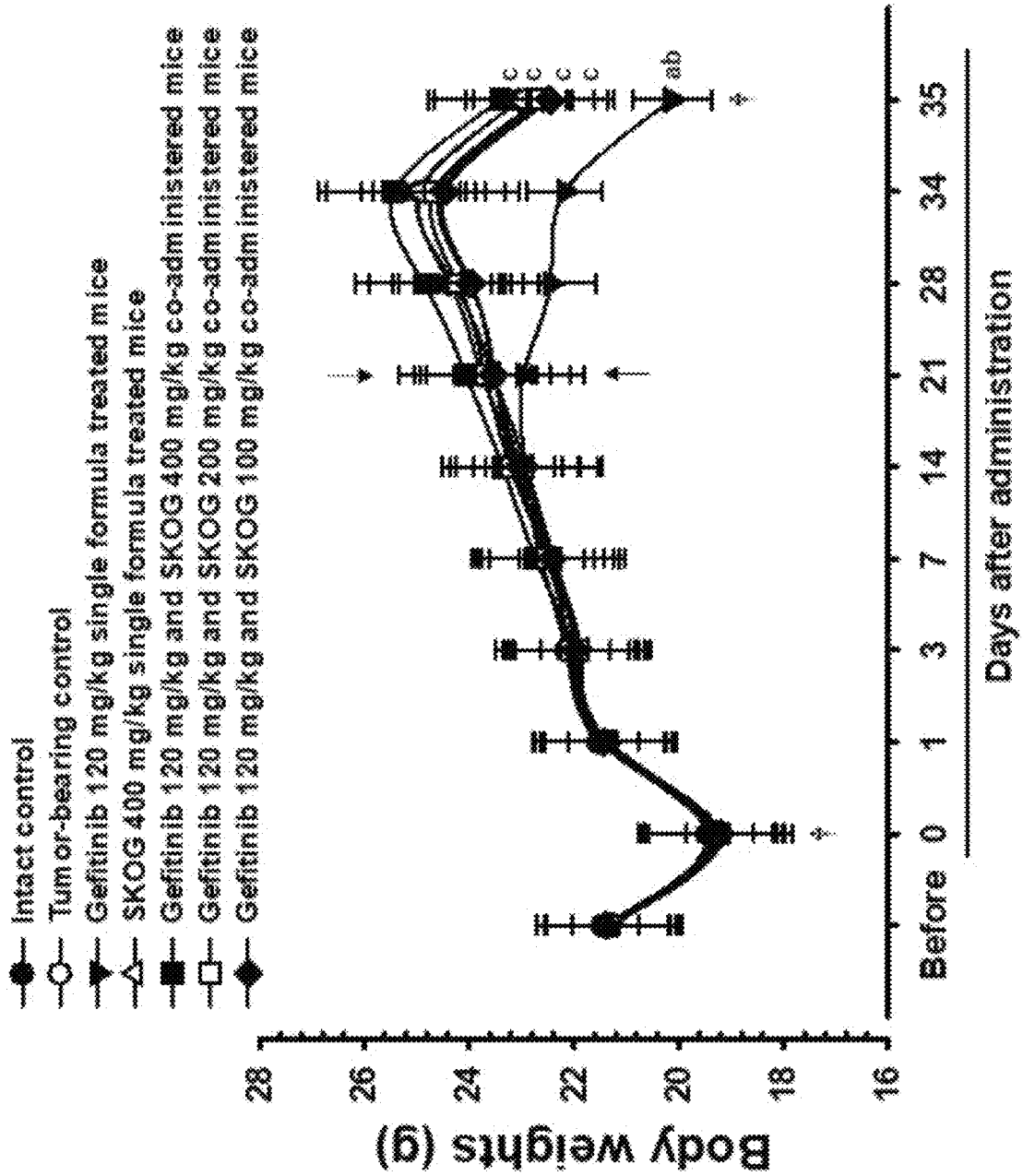
FIG. 5 shows changes in body weight of tumor cell xenograft mice according to SKOG or gefitinib single administration and SKOG and gefitinib co-administration.

The tumor xenograft control group showed no significant change in body weight during the entire experimental period compared with the normal medium control group, but showed a significant reduction in actual body weight excluding tumor weight and a reduction in weight gain during the administration period on the basis of the actual body weight compared with the normal medium control group ($p<0.01$). The gefitinib single administered group showed a significant reduction in body weight from 28 days after the administration compared with the tumor xenograft control group (p<0.01), and significant reductions in actual body weight and weight gain during the administration period on the basis of the actual body weight compared with the normal medium control group (p<0.01 or p<0.05). The composition (*Adenophorae triphylla, Panax ginseng, Wolfiporia extensa, Rehmannia glutinosa*, and mel being mixed, SKOG) single administered group, the gefitinib 120 mg/kg and composition (*Adenophorae triphylla, Panax ginseng, Wolfiporia extensa, Rehmannia glutinosa*, and mel being mixed) 400, 200, and 100 mg/kg co-administered (GSK 400, 200, and 100 mg/kg) groups showed significant increases in actual body weight and weight gain compared with the tumor xenograft control group (p<0.01 or p<0.05). In particular, the gefitinib 120 mg/kg group and the GSK 400, 200, and 100 mg/kg groups showed a significant increase in body weight from 28 days after the administration compared with gefitinib 120 mg/kg single administered group (p<0.01), also showed significant increases in actual body weight and weight gain compared with the gefitinib 120 mg/kg single administered group (p<0.01) (Table 5 and FIG. 5). The superscript alphabets indicate significant differences. The presence of the same letter means that there is significance between the experimental groups.

of administration compared with the tumor xenograft control group (p<0.01), and a significant reduction in tumor volume during the administration period compared with the tumor xenograft control group (p<0.01). The SKOG 400 mg/kg single administered group also showed a significant reduction in tumor volume from day 14 after the start of administration compared with the tumor xenograft control group (p<0.01). The change in tumor volume during the administration period was showed to be significant reduction compared with the tumor xenograft control group (p<0.01). The GSK 400, 200, and 100 mg/kg administered groups also showed significant reductions from 14 days after the start of administration compared with the tumor xenograft control group (p<0.01 or p<0.05), and thus showed significant reductions in tumor volume during the administration period compared with the tumor xenograft control group (p<0.01). Especially, the GSK 400 mg/kg administered group, from 14 days after the start of administration, and the GSK 200 mg/kg and 100 mg/kg administration groups from 21 days after the start of administration showed significant reductions in tumor volume compared with the gefitinib single administered group (p<0.01 or p<0.05), and also showed significant reductions in tumor volume during the period

TABLE 5

| Group | Body weight (g) | | | |
|---|---|---|---|---|
| | Administration initiation | Sacrifice | Actual body weight | Weight gain (g) |
| Control group | | | | |
| Intact | 19.45 ± 1.31 | 23.04 ± 0.88 | 23.04 ± 0.88 | 3.59 ± 0.56 |
| TB | 19.43 ± 1.24 | 22.58 ± 0.47 | 19.77 ± 0.63$^a$ | 0.34 ± 0.90$^a$ |
| Single material administered group | | | | |
| Gefitinib | 19.29 ± 1.29 | 20.13 ± 0.76$^{fg}$ | 18.46 ± 0.77$^{ad}$ | −0.83 ± 0.98$^{ac}$ |
| SKOG | 19.38 ± 1.39 | 23.03 ± 1.65$^{gh}$ | 20.99 ± 1.59$^{ade}$ | 1.61 ± 0.67$^{ace}$ |
| Gefitinib and SKOG co-administered group (within 5 min) | | | | |
| 400 mg/kg | 19.33 ± 1.34 | 23.40 ± 1.37$^h$ | 22.93 ± 1.44$^{ce}$ | 3.60 ± 0.71$^{ce}$ |
| 200 mg/kg | 19.23 ± 1.41 | 22.65 ± 1.42$^h$ | 21.94 ± 1.42$^{ce}$ | 2.72 ± 0.45$^{bc}$ |
| 100 mg/kg | 19.20 ± 0.64 | 22.45 ± 0.85$^h$ | 21.19 ± 0.90$^{ade}$ | 1.99 ± 0.65$^{ace}$ |

As for the actual body weight excluding tumor weight on the final sacrifice day, the tumor xenograft control group showed a change in −14.20% compared with the normal medium control group, and the gefitinib 120 mg/kg and SKOG 400 mg/kg single administration group and the gefitinib 120 mg/kg and SKOG 400, 200, and 100 mg/kg co-administered groups showed changes of −6.61, 6.18, 15.99, 11.01, and 7.20% compared with the tumor xenograft group.

As for the weight gain during the administration period on the basis of the actual body weight (for 35 days; actual body weight excluding tumor weight on the final sacrifice day–body weight on the start day of administration), the tumor xenograft control group showed a change of −90.47% compared with the normal medium control group, and the gefitinib 120 mg/kg and SKOG 400 mg/kg single administered groups and the GSK 400, 200, and 100 mg/kg administered groups showed changes of −341.95, 372.28, 954.35, 695.50, and 482.41%, respectively, compared with the tumor xenograft control group.

(6) Change in Tumor Volume

Figure 6:
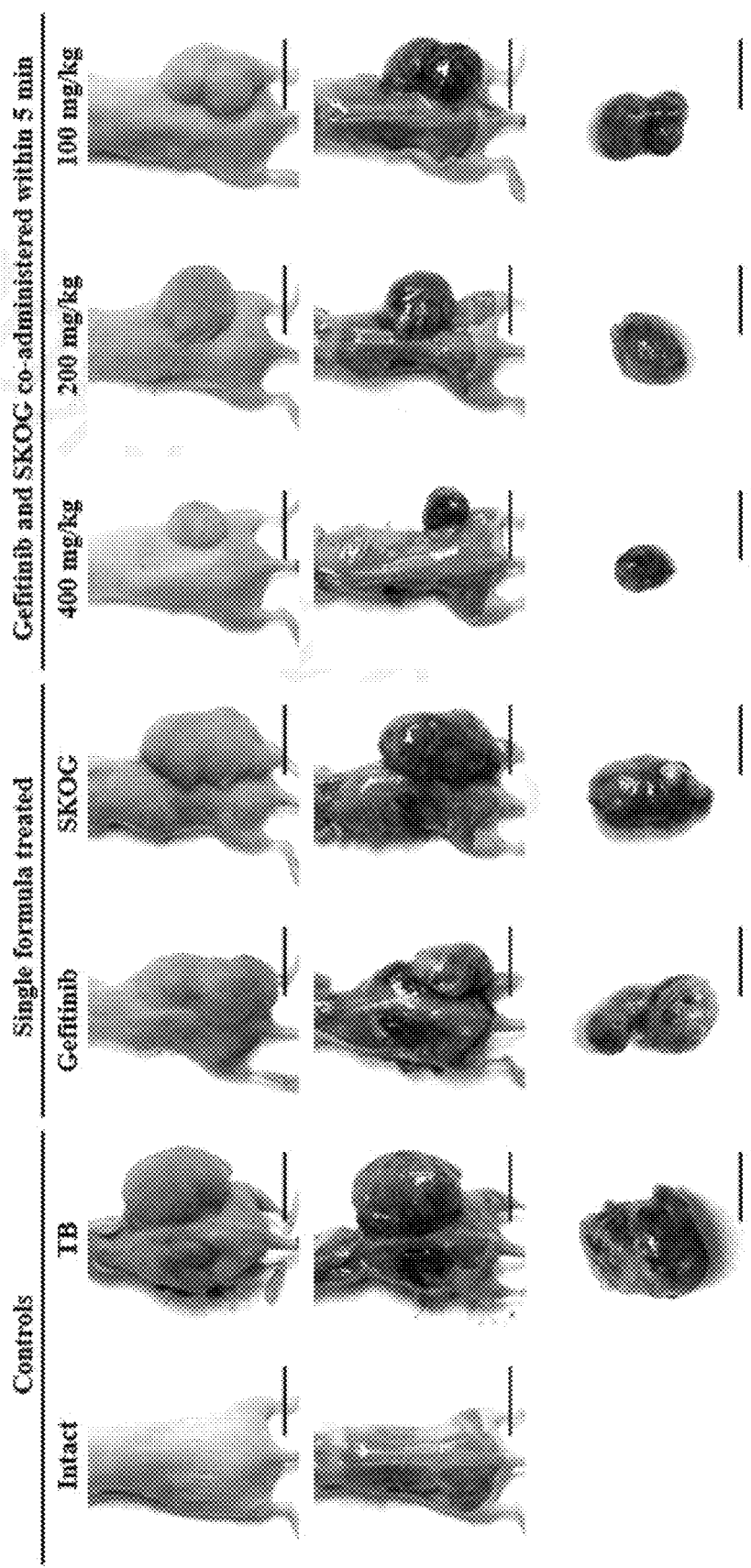
FIG. 6 shows images of the tumor size in tumor cell xenograft mice according to SKOG or gefitinib single administration and SKOG and gefitinib co-administration.
Figure 7:
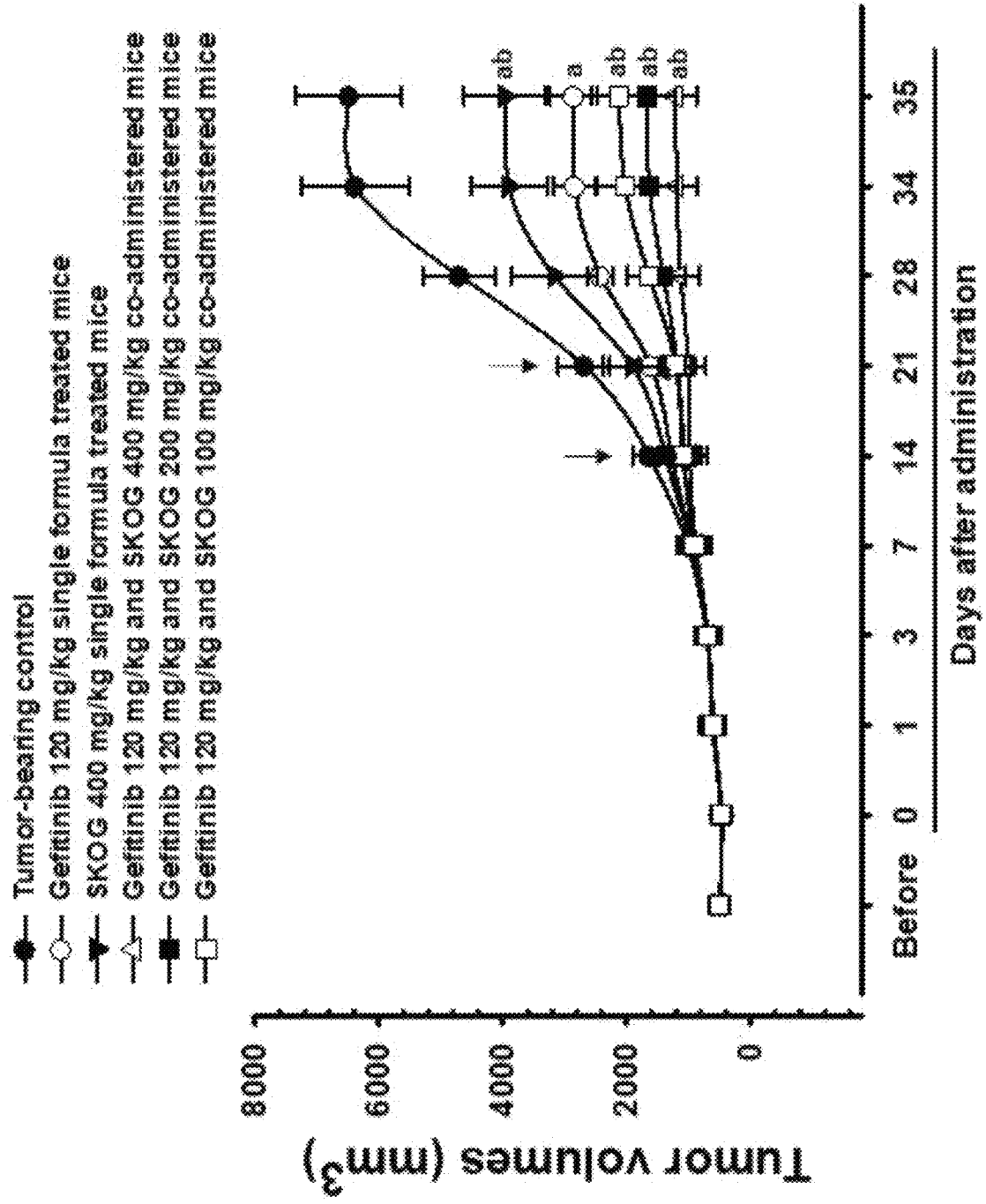
FIG. 7 shows tumor volumes of tumor cell xenograft mice according to SKOG or gefitinib single administration and SKOG and gefitinib co-administration.

The gefitinib single administered group showed a significant reduction in tumor volume from day 14 after the start section compared with the gefitinib single administered group (p<0.01) (Table 6, FIGS. 6 and 7).

TABLE 6

| Groups | Tumor volume (mm³) | | |
|---|---|---|---|
| | Start of administration [A] | At the time of sacrifice [B] | Change (mm³) [B − A] |
| Control group | | | |
| TB | 469.02 ± 102.47 | 6487.36 ± 862.66 | 6018.34 ± 774.83 |
| Single material administered group | | | |
| Gefitinib | 462.10 ± 105.87 | 2858.51 ± 377.01$^a$ | 2396.41 ± 329.84$^a$ |
| SKOG | 472.89 ± 141.15 | 3972.27 ± 655.53$^{ab}$ | 3499.37 ± 557.32$^{ab}$ |
| Gefitinib and SKOG co-administered group (within 5 min) | | | |
| 400 mg/kg | 473.39 ± 137.02 | 1209.50 ± 335.04$^{ab}$ | 736.11 ± 235.75$^{ab}$ |
| 200 mg/kg | 477.76 ± 161.99 | 1670.83 ± 471.94$^{ab}$ | 1193.07 ± 375.71$^{ab}$ |
| 100 mg/kg | 475.73 ± 122.90 | 2125.75 ± 442.71$^{ab}$ | 1650.02 ± 431.10$^{ab}$ |

As for a change in tumor volume during the drug administration period (for five weeks; tumor volume on the final sacrifice day–tumor volume on the start day of administration), the gefitinib 120 mg/kg and SKOG 400 mg/kg single administered groups and the GSK 400, 200, and 100 mg/kg administered groups showed changes of −60.18, −41.85, −87.77, −80.18, and −72.58%, respectively, compared with the tumor xenograft control group.

(7) Change in Tumor Weight

All the drug administered groups showed significant reductions (p<0.01) in tumor relative and absolute weights compared with the tumor xenograft control group. Especially, the GSK 400, 200, and 100 mg/kg groups showed significant reductions in absolute weight (Table 7) and relative weight (Table 9) compared with gefitinib 120 mg/kg single administered group (p<0.01 or p<0.05) (Tables 7 and 8 and FIG. 6).

(p<0.01). The gefitinib single administered group showed no changes in absolute and relative spleen weights compared with the tumor xenograft control group (Tables 7 and 8).

As for the absolute spleen weight, the tumor xenograft control group showed a change of 50.62% compared with the normal medium control group, and the gefitinib 120 mg/kg and SKOG 400 mg/kg single administered groups and the GSK 400, 200, and 100 mg/kg administered groups showed changes of −7.13, 46.44, 88.74, 79.08, and 51.03% compared with the tumor xenograft control group, respectively.

As for the relative spleen weight, the tumor xenograft control group showed a change of 49.67% compared with the normal medium control group, and the gefitinib 120

TABLE 7

| Group | Tumor weight | Spleen | Submandibular lymph nodes | Periovarian fat |
|---|---|---|---|---|
| Control group | | | | |
| Intact | — | 0.110 ± 0.011 | 0.013 ± 0.004 | 0.050 ± 0.013 |
| TB | 2.808 ± 0.282 | 0.054 ± 0.005$^a$ | 0.004 ± 0.001$^d$ | 0.008 ± 0.002$^d$ |
| Single material administered group | | | | |
| Gefitinib | 1.664 ± 0.292$^f$ | 0.051 ± 0.007$^a$ | 0.004 ± 0.001$^d$ | 0.007 ± 0.002$^d$ |
| SKOG | 2.036 ± 0.249$^f$ | 0.080 ± 0.008$^{abc}$ | 0.008 ± 0.002$^{d/g}$ | 0.024 ± 0.004$^{d/g}$ |
| Gefitinib and SKOG co-administered group (within 5 min) | | | | |
| 400 mg/kg | 0.472 ± 0.130$^{f/g}$ | 0.103 ± 0.011$^{bc}$ | 0.011 ± 0.002$^{f/g}$ | 0.033 ± 0.007$^{d/g}$ |
| 200 mg/kg | 0.706 ± 0.278$^{f/g}$ | 0.097 ± 0.008$^{abc}$ | 0.010 ± 0.002$^{f/g}$ | 0.028 ± 0.006$^{d/g}$ |
| 100 mg/kg | 1.260 ± 0.198$^{f/h}$ | 0.082 ± 0.012$^{abc}$ | 0.009 ± 0.001$^{e/g}$ | 0.024 ± 0.005$^{d/g}$ |

TABLE 8

| Group | Tumor weight | Spleen | submandibular lymph nodes | Periovarian fat |
|---|---|---|---|---|
| Control group | | | | |
| Intact | — | 0.479 ± 0.060 | 0.057 ± 0.017 | 0.216 ± 0.051 |
| TB | 12.453 ± 1.378 | 0.241 ± 0.028$^a$ | 0.019 ± 0.007$^e$ | 0.037 ± 0.008$^e$ |
| Single material administered group | | | | |
| Gefitinib | 8.274 ± 1.443$^g$ | 0.251 ± 0.036$^a$ | 0.019 ± 0.006$^e$ | 0.036 ± 0.011$^e$ |
| SKOG | 8.857 ± 1.042$^g$ | 0.347 ± 0.043$^{acd}$ | 0.034 ± 0.009$^{egh}$ | 0.104 ± 0.020$^{egh}$ |
| Gefitinib and SKOG co-administered group (within 5 min) | | | | |
| 400 mg/kg | 2.037 ± 0.632$^{gh}$ | 0.440 ± 0.050$^{cd}$ | 0.048 ± 0.010$^{gh}$ | 0.140 ± 0.035$^{egh}$ |
| 200 mg/kg | 3.123 ± 1.208$^{gh}$ | 0.430 ± 0.029$^{bcd}$ | 0.044 ± 0.005$^{gh}$ | 0.125 ± 0.031$^{egh}$ |
| 100 mg/kg | 5.623 ± 0.961$^{gh}$ | 0.365 ± 0.042$^{acd}$ | 0.039 ± 0.005$^{fgh}$ | 0.105 ± 0.020$^{egh}$ |

The gefitinib 120 mg/kg and SKOG 400 mg/kg single administered groups and the GSK 400, 200, and 100 mg/kg administered groups showed changes in absolute tumor weight of −40.73, −27.50, −83.20, −74.85, and −55.15%, respectively, and changes in relative tumor weight of −33.56, −28.88, −83.64, −74.92, and −54.84%, respectively, compared with the tumor xenograft control group.

(8) Change in Spleen Weight

The tumor xenograft control group showed significant reductions in absolute and relative spleen weights compared with the normal medium control group (p<0.01), but the SKOG 400 mg/kg single administered group and the GSK 400, 200, and 100 mg/kg administered groups showed significant increases in weight compared with the tumor xenograft control group (p<0.01). Especially, the GSK 400, 200, and 100 mg/kg administered groups showed significant increases in absolute and relative spleen weights compared with the gefitinib single administered group, respectively mg/kg and SKOG 400 mg/kg single administered groups and the GSK 400, 200, and 100 mg/kg administered groups showed changes of 4.11, 43.99, 82.15, 78.32, and 51.23% compared with the tumor xenograft control group, respectively.

(9) Change in Submandibular Lymph Node Weight

The tumor xenograft control group showed significant reductions in absolute and relative submandibular lymph node weights compared with the normal medium control group, respectively (p<0.01), but the SKOG 400 mg/kg single administered group and the GSK 400, 200, and 100 mg/kg administered groups showed significant increases in submandibular lymph node weight compared with the tumor xenograft control group, respectively (p<0.01). Especially, the GSK 400, 200, and 100 mg/kg administered groups showed significant increases in absolute and relative submandibular lymph node weights compared with the gefitinib single administered group (p<0.01). The gefitinib 120 mg/kg single administered group showed no change in submandibular lymph node weight compared with the tumor xenograft control group (Tables 7 and 8).

The tumor xenograft control group showed changes in absolute and relative submandibular lymph node weights of −67.92 and −67.03% compared with the normal medium control group. The gefitinib 120 mg/kg and SKOG 400 mg/kg single administered groups and the GSK 400, 200, and 100 mg/kg administered groups showed changes in absolute submandibular lymph node weight of −8.82, 85.29, 161.76, 132.35, and 105.88% compared with the tumor xenograft control group, respectively, and changes in relative submandibular lymph node weight of 1.85, 81.72, 151.99, 130.57, and 106.38% compared with the tumor xenograft control group, respectively.

(10) Change in Periovarian Fat Weight

The tumor xenograft control group showed significant reductions in absolute and relative periovarian fat weights compared with the normal medium control group (p<0.01), but the SKOG single administered group and all the three SKOG and gefitinib co-administered groups showed significant increases in periovarian fat weight compared with the tumor xenograft control group (p<0.01). Especially, the GSK 400, 200, and 100 mg/kg administered groups showed significant increases in periovarian fat weight compared with the gefitinib single administered group, respectively (p<0.01). The gefitinib 120 mg/kg single administered group showed no changes in absolute and relative periovarian accumulation fat weights compared with the tumor xenograft control group (Tables 7 and 8).

As for the absolute periovarian fat weight, the tumor xenograft control group showed a change of −83.21% compared with the normal medium control group. The gefitinib 120 mg/kg and SKOG 400 mg/kg single administered groups and the GSK 400, 200, and 100 mg/kg administered groups showed changes of −13.43, 183.58, 288.06, 237.31, and 182.09%, respectively, compared with the tumor xenograft control group, respectively, and changes of −13.43, 183.58, 288.06, 237.31, and 182.09%, respectively, compared with the tumor xenograft control group.

As for the relative periovarian fat weight, the tumor xenograft control group showed a change of −82.80% compared with the normal medium control group. The gefitinib 120 mg/kg and SKOG 400 mg/kg single administered groups and the GSK 400, 200, and 100 mg/kg administered groups showed changes of −2.79, 178.96, 277.38, 237.62, and 183.23%, respectively, compared with the tumor xenograft control group.

(11) Changes in Serum IL-6 and IFN-γ Levels

Figure 8:
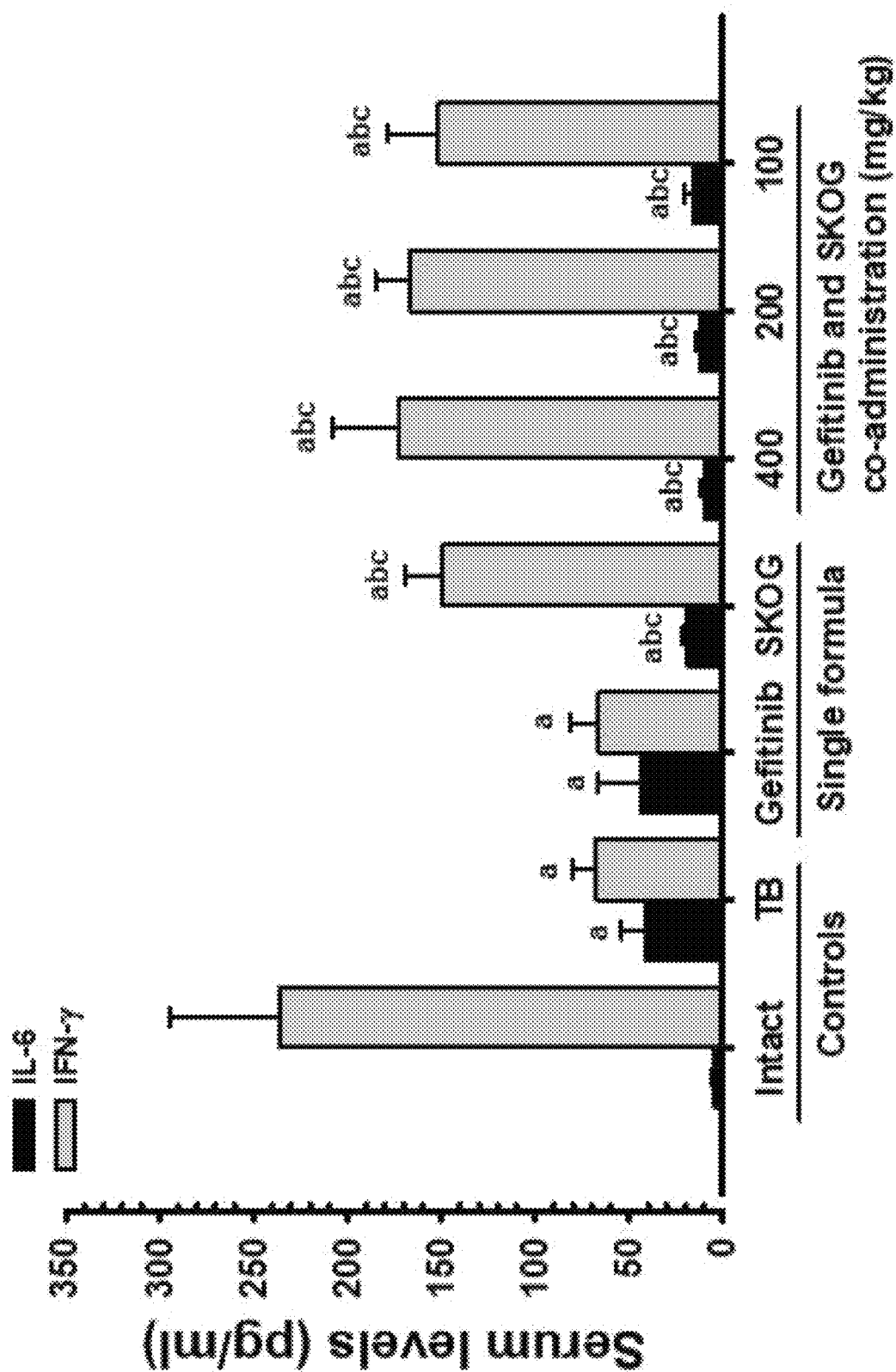
FIG. 8 shows serum IL-6 and IFN-γ levels in tumor cell xenograft mice according to SKOG or gefitinib single administration and SKOG and gefitinib co-administration.

The tumor xenograft control group showed a significant increase in serum IL-6 level (p<0.01) and a significant reduction in IFN-γ level (p<0.01), compared with the normal medium control group. However, the SKOG 400 mg/kg single composition group and the GSK 400, 200, and 100 mg/kg administered groups showed a significant reduction in serum IL-6 level and a significant increase in IFN-γ level compared with the tumor xenograft control group (p<0.01). Especially, the GSK 400, 200, and 100 mg/kg administered groups showed a significant reduction in serum IL-6 level and a significant increase in IFN-γ level compared with the gefitinib single administered group (p<0.01). The gefitinib single administered group showed no significant changes in serum IL-6 and IFN-γ levels compared with the tumor xenograft control group (FIG. 8).

As for the serum IL-6 level, the tumor xenograft control group showed a change of 825.11% compared with the normal medium control group, and the gefitinib 120 mg/kg and SKOG 400 mg/kg single administered groups and the GSK 400, 200, and 100 mg/kg administered groups showed changes of 6.25, −53.28, −76.52, −70.72, and −60.87%, respectively, compared with the tumor xenograft control group.

As for the serum IFN-γ level, the tumor xenograft control group showed a change of −71.06% compared with the normal medium control group, and the gefitinib 120 mg/kg and SKOG 400 mg/kg single administered groups and the GSK 400, 200, and 100 mg/kg administered groups showed changes of −2.85, 118.57, 151.53, 142.93, and 121.95%, respectively, compared with the tumor xenograft control group.

(12) Change in NK Cell Activity

Figure 9:
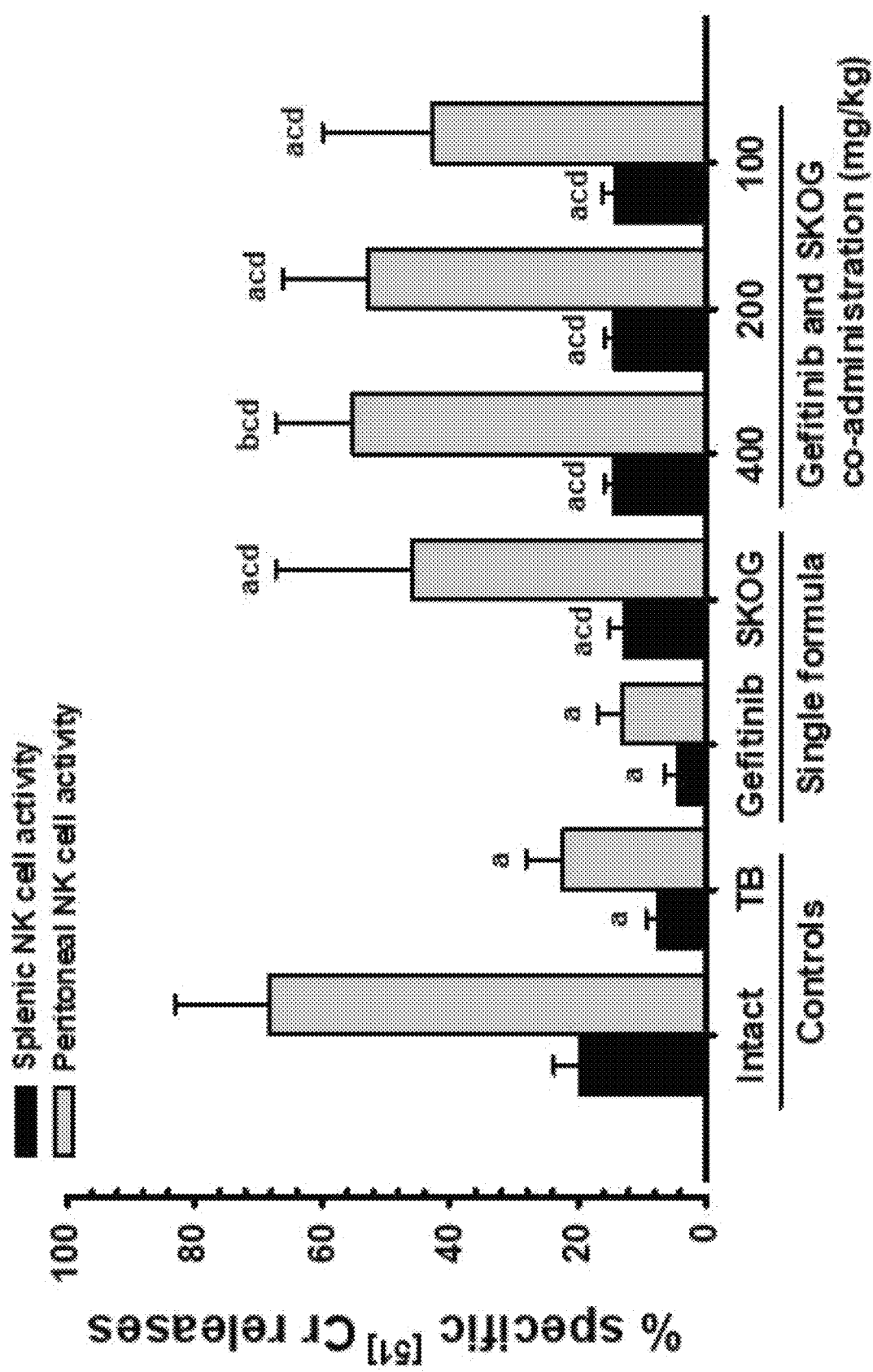
FIG. 9 shows splenic and peritoneal NK cell activity in tumor cell xenograft mice according to SKOG or gefitinib single administration and SKOG and gefitinib co-administration.

The tumor xenograft control group showed a significant reduction in splenic and peritoneal NK cell activities compared with the normal medium control group (p<0.01). However, the SKOG 400 mg/kg single composition group and the GSK 400, 200, and 100 mg/kg administered groups showed significant increases in splenic and peritoneal NK cell activities compared with the tumor xenograft control group (p<0.01). Especially, the SKOG 400 mg/kg single composition group and the GSK 400, 200, and 100 mg/kg administered groups showed significant increases in splenic and peritoneal NK cell activities compared with the gefitinib single administered group (p<0.01). The gefitinib single administered group showed no significant changes in splenic and peritoneal NK cell activities compared with the tumor xenograft control group (FIG. 9).

As for the splenic NK cell activity, the tumor xenograft control group showed a change of −82.17% compared with the normal medium control group, and the gefitinib 120 mg/kg and SKOG 400 mg/kg single administered groups and the GSK 400, 200, and 100 mg/kg administered groups showed changes of −6.32, 110.42, 207.47, 157.93, and 116.80%, respectively, compared with the tumor xenograft control group.

As for the peritoneal NK cell activity, the tumor xenograft control group showed a change of −81.83% compared with the normal medium control group, and the gefitinib 120 mg/kg and SKOG 400 mg/kg single administered groups and the GSK 400, 200, and 100 mg/kg administered groups showed changes of −7.43, 151.48, 279.65, 207.54, and 149.50%, respectively, compared with the tumor xenograft control group.

(13) Change in Splenic Cytokin Levels

The tumor xenograft control group showed significant reductions in splenic TNF-α, IL-1β, and IL-10 levels compared with the normal medium control group (p<0.01). However, the SKOG 400 mg/kg single composition group and the GSK 400, 200, and 100 mg/kg administered groups showed significant increases in splenic cytokine levels compared with the tumor xenograft control group (p<0.01). Especially, the GSK 400, 200, and 100 mg/kg administered groups showed significant increases in splenic TNF-α, IL-1β, and IL-10 levels, respectively, compared with the gefitinib single administered group (p<0.01). The gefitinib single administered group showed no significant changes in splenic cytokine levels compared with the tumor xenograft control group (Table 9).

TABLE 9

| Group | TNF-α (Tumor necrosis factor-α) | IL-1β (Interleukin-1β) | IL-10 (Interleukin-10) |
|---|---|---|---|
| Control group | | | |
| Intact | 142.83 ± 49.08 | 48.33 ± 19.26 | 122.81 ± 34.71 |
| TB | 26.29 ± 10.73$^a$ | 8.64 ± 3.05$^a$ | 26.52 ± 12.47$^a$ |
| Single material administered group | | | |
| Gefitinib | 26.23 ± 10.81$^a$ | 8.36 ± 1.96$^a$ | 25.58 ± 11.94$^a$ |
| SKOG | 70.03 ± 38.12$^{acd}$ | 30.26 ± 12.78$^{bcd}$ | 73.46 ± 19.50$^{acd}$ |
| Gefitinib and SKOG co-administered group (wtihin 5 min) | | | |
| 400 mg/kg | 98.80 ± 26.02$^{cd}$ | 44.35 ± 10.11$^{cd}$ | 97.56 ± 26.24$^{cd}$ |
| 200 mg/kg | 81.62 ± 24.83$^{acd}$ | 37.41 ± 12.06$^{cd}$ | 82.83 ± 22.96$^{bcd}$ |
| 100 mg/kg | 71.75 ± 25.06$^{acd}$ | 29.51 ± 12.75$^{bcd}$ | 72.39 ± 12.62$^{acd}$ |

As for the splenic TNF-α level, the tumor xenograft control group showed a change of −81.59% compared with the normal medium control group, and the gefitinib 120 mg/kg and SKOG 400 mg/kg single administered groups and the GSK 400, 200, and 100 mg/kg administered groups showed changes of −0.24, 166.39, 275.84, 210.48, and 172.94%, respectively, compared with the tumor xenograft control group.

As for the splenic IL-1β level, the tumor xenograft control group showed a change of −82.12% compared with the normal medium control group, and the gefitinib 120 mg/kg and SKOG 400 mg/kg single administered groups and the GSK 400, 200, and 100 mg/kg administered groups showed changes of −3.18, 250.31, 413.34, 333.05, and 241.56%, respectively, compared with the tumor xenograft control group.

As for the splenic IL-10 level, the tumor xenograft control group showed a change of −78.41% compared with the normal medium control group, and the gefitinib 120 mg/kg and SKOG 400 mg/kg single administered groups and the GSK 400, 200, and 100 mg/kg administered groups showed changes of −3.53, 177.04, 267.95, 212.40, and 173.00%, respectively, compared with the tumor xenograft control group.

(14) Histological changes (1) Histopathological Change of Tumor Mass

Figure 10:
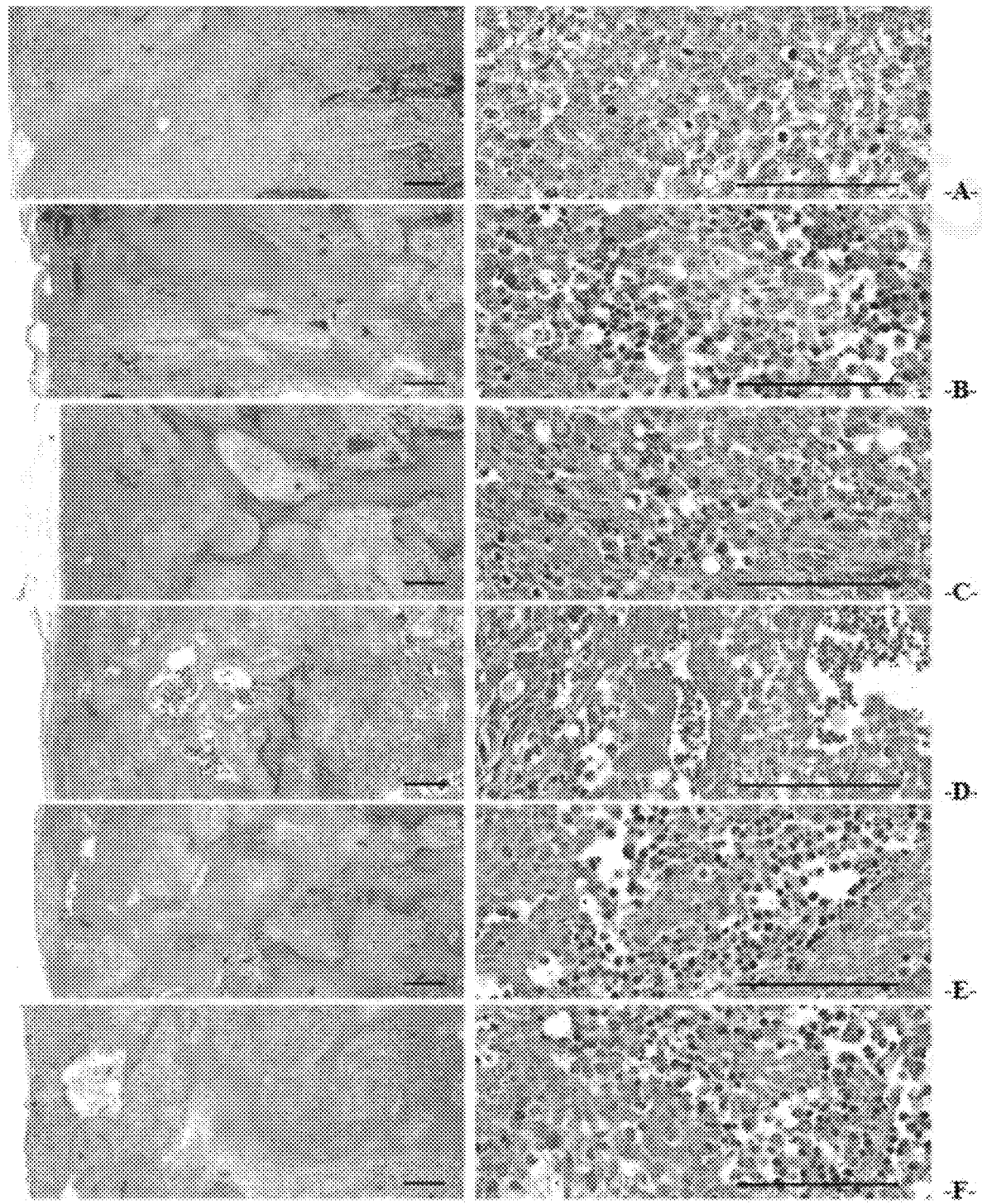
FIG. 10 shows cross-sectional images of the tumor mass in tumor cell xenograft mice according to SKOG or gefitinib single administration and SKOG and gefitinib co-administration.

In the tumor xenograft control group, comparatively well differentiated NCI-H520 lung cancer cells were densely formed, a cytoplasmic eosinophilic increase and karyopyknosis by apoptosis were found, and mitosis was also frequently observed. The gefitinib 120 mg/kg and SKOG 400 mg/kg single administered groups and the GSK 400, 200, and 100 mg/kg administered groups showed a significant increase in apoptotic cells (p<0.01) and a significant reduction in proportion of NCI-H520 cells (p<0.01). Especially, the GSK 400, 200, and 100 mg/kg administered groups showed a significant reduction in tumor cell volume and a significant increase in the number of apoptotic cells, compared with the gefitinib single administered group (p<0.01) (Table 10 and FIG. 10).

TABLE 10

| group | Tumor cell volume (%/mm$^2$) | Percentage of apoptotic cells (%) | Percentage of immune-responsive cells (%/tumor cells) | | | | |
|---|---|---|---|---|---|---|---|
| | | | Caspase-3 | PARP | COX-2 | iNOS | TNF-α |
| Control group | | | | | | | |
| TB | 79.27 ± 8.85 | 7.56 ± 3.59 | 11.01 ± 2.81 | 14.52 ± 6.32 | 59.83 ± 10.29 | 12.13 ± 4.23 | 7.76 ± 1.66 |
| Single material administered group | | | | | | | |
| Gefitinib | 56.28 ± 7.19$^a$ | 49.88 ± 8.53$^a$ | 40.60 ± 11.72$^d$ | 46.98 ± 10.22$^a$ | 38.89 ± 5.69$^d$ | 12.07 ± 5.40 | 7.28 ± 2.74 |
| SKOG | 66.24 ± 5.75$^a$ | 30.82 ± 5.08$^a$ | 28.77 ± 6.58$^{df}$ | 35.84 ± 10.63$^{ac}$ | 39.01 ± 13.59$^d$ | 37.16 ± 10.24$^{ab}$ | 37.05 ± 11.47$^{de}$ |
| Gefitinib and SKOG co-administered group (within 5 min) | | | | | | | |
| 400 mg/kg | 29.13 ± 8.75$^{ab}$ | 86.63 ± 7.29$^{ab}$ | 75.42 ± 10.45$^{de}$ | 86.29 ± 5.22$^{ab}$ | 11.88 ± 2.99$^{de}$ | 74.13 ± 10.12$^{ab}$ | 62.21 ± 17.33$^{de}$ |
| 200 mg/kg | 38.59 ± 7.28$^{ab}$ | 75.19 ± 8.18$^{ab}$ | 67.61 ± 12.98$^{de}$ | 73.59 ± 10.57$^{ab}$ | 20.69 ± 5.09$^{de}$ | 63.79 ± 11.92$^{ab}$ | 54.51 ± 12.48$^{de}$ |
| 100 mg/kg | 45.75 ± 5.23$^{ab}$ | 65.37 ± 10.60$^{ab}$ | 56.78 ± 9.36$^{df}$ | 62.96 ± 7.65$^{ab}$ | 28.77 ± 7.32$^{df}$ | 41.65 ± 11.51$^{ab}$ | 41.97 ± 13.30$^{de}$ |

Figure 11:
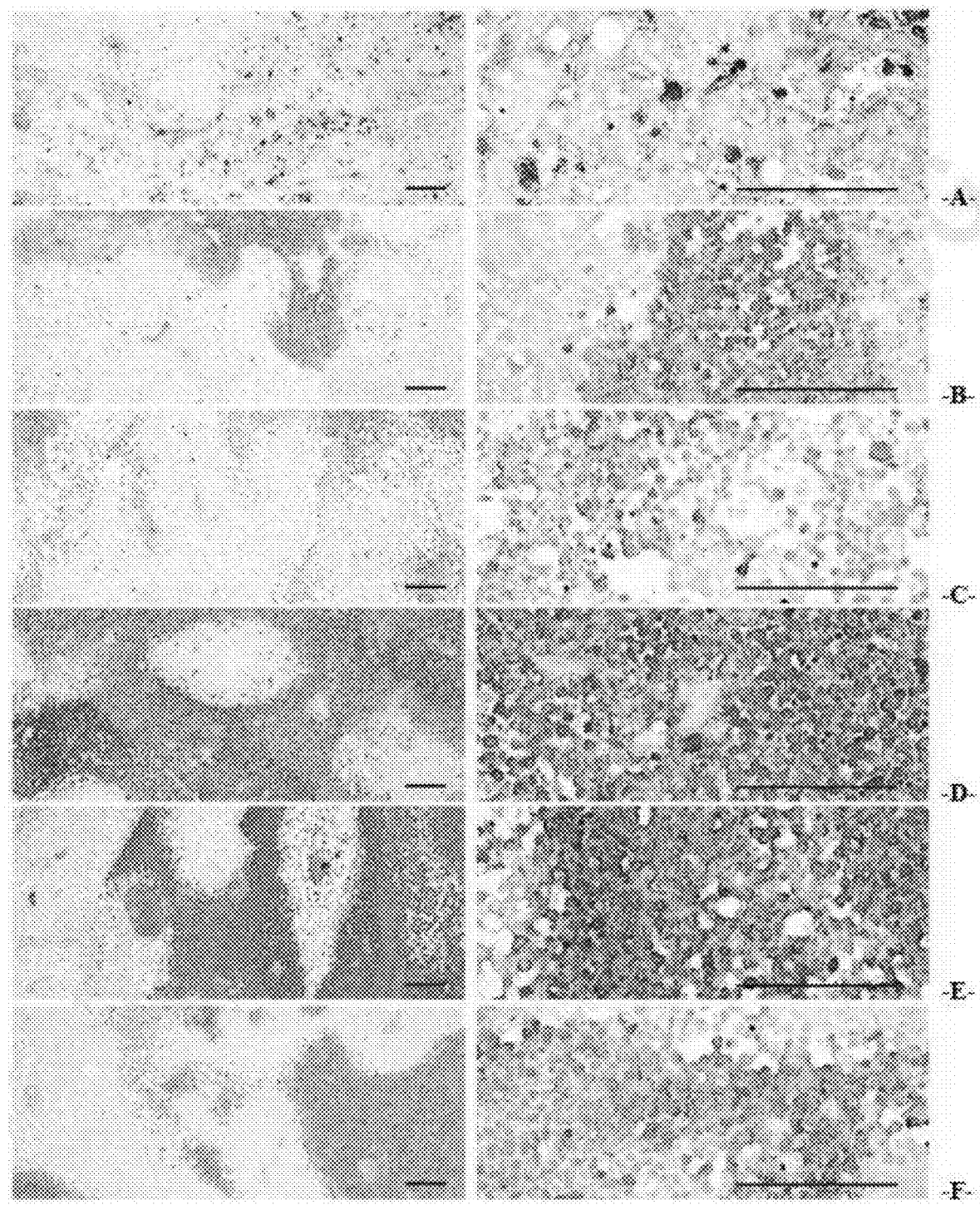
Figure 12:
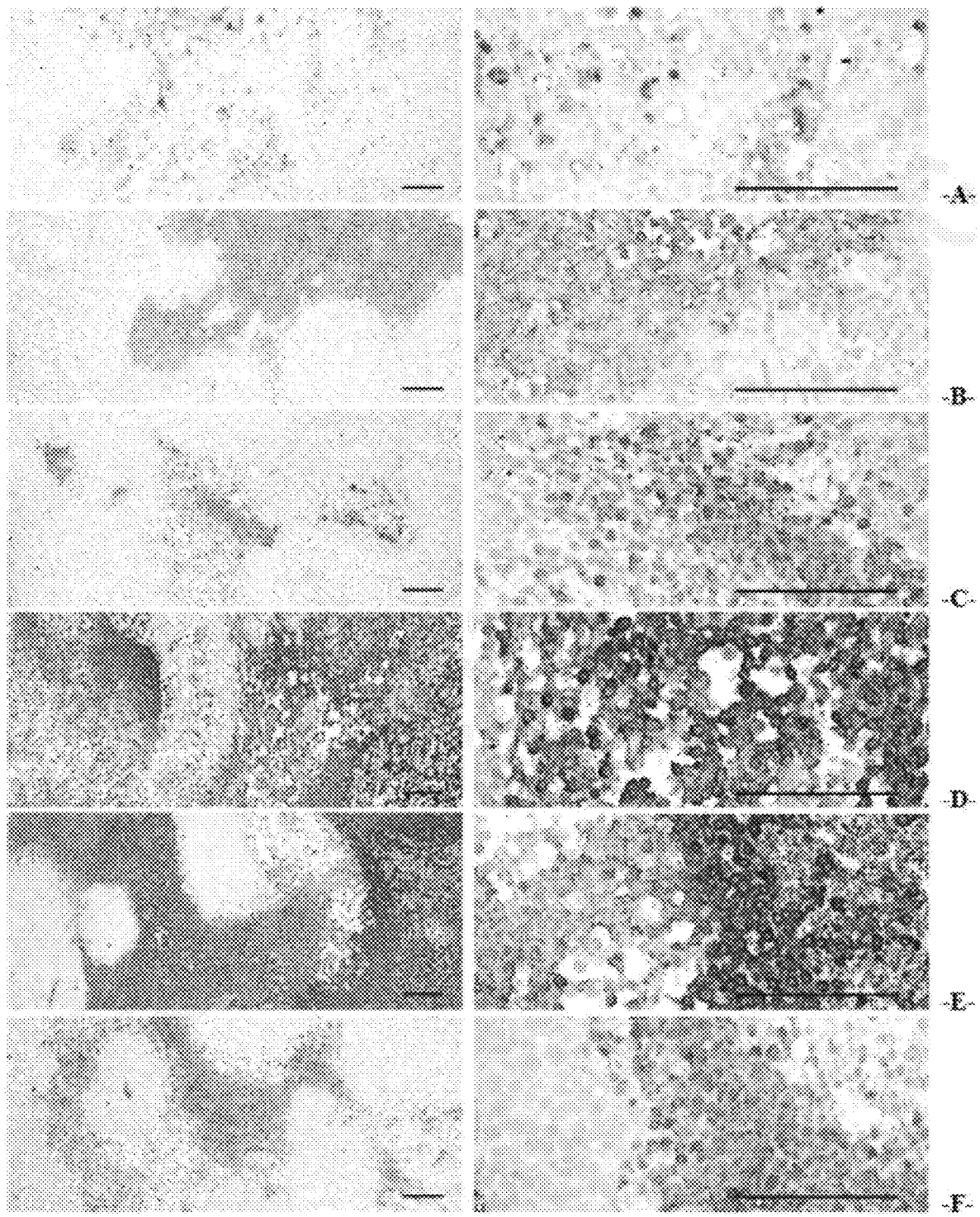
Figure 13:
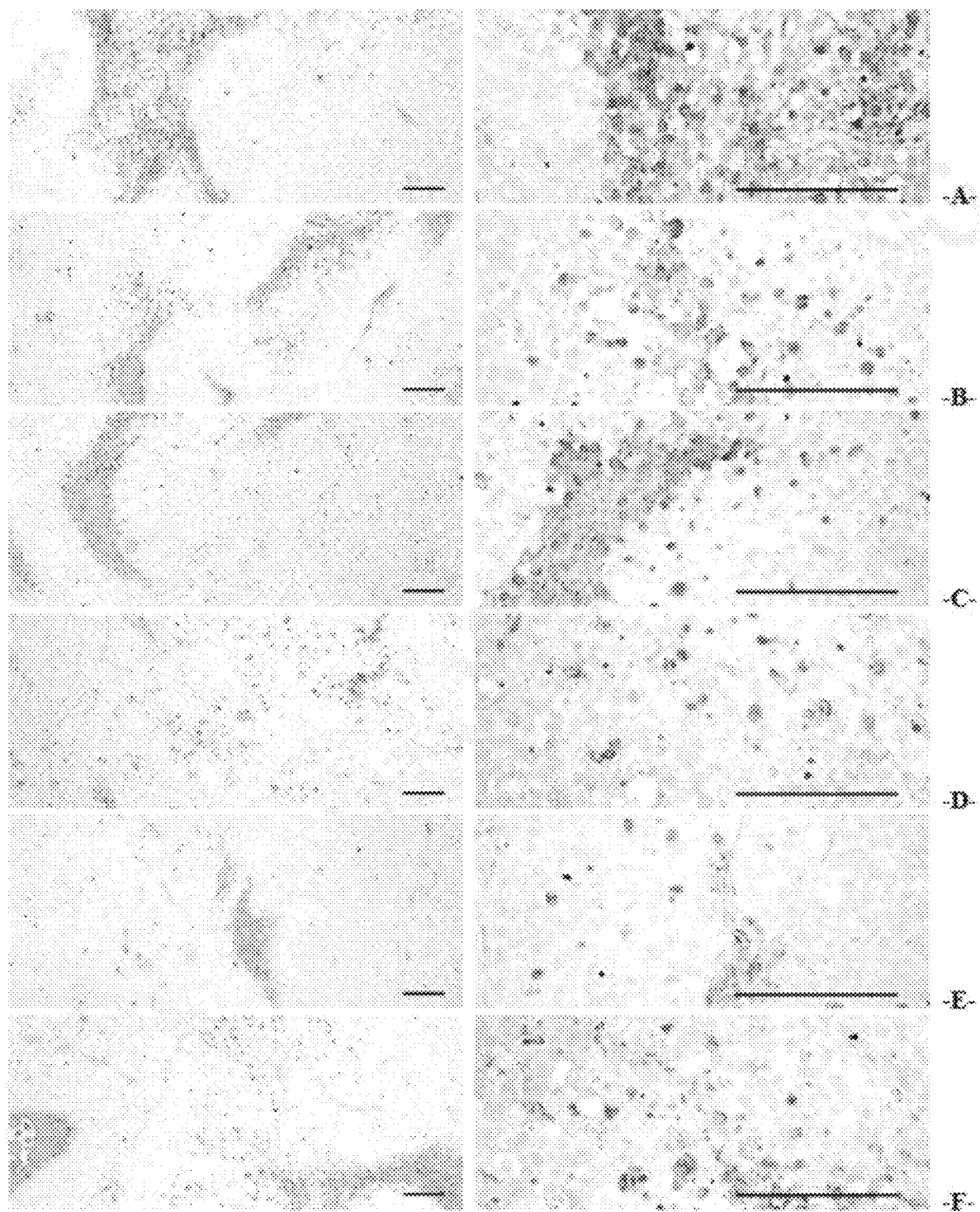
Figure 14:
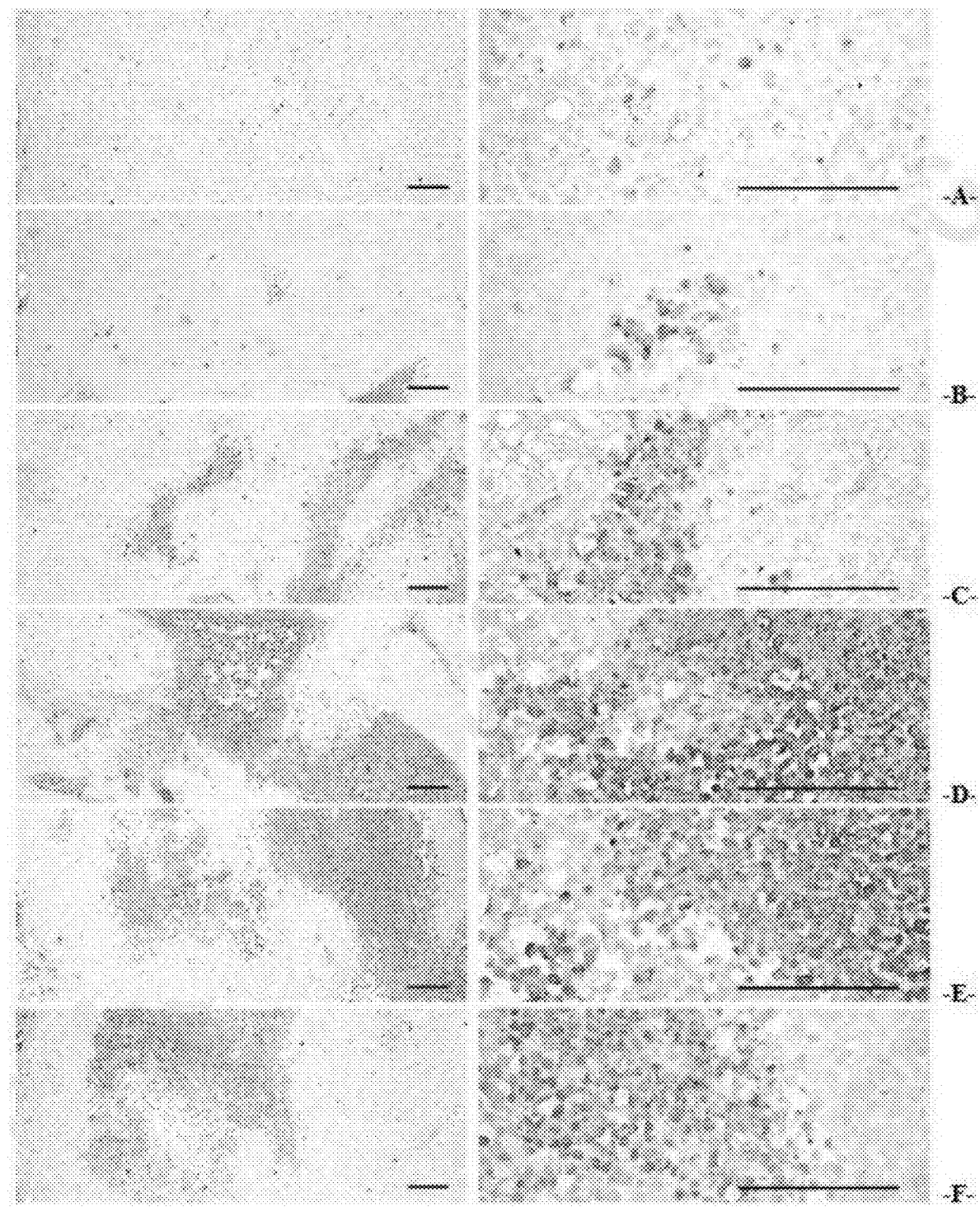
Figure 15:
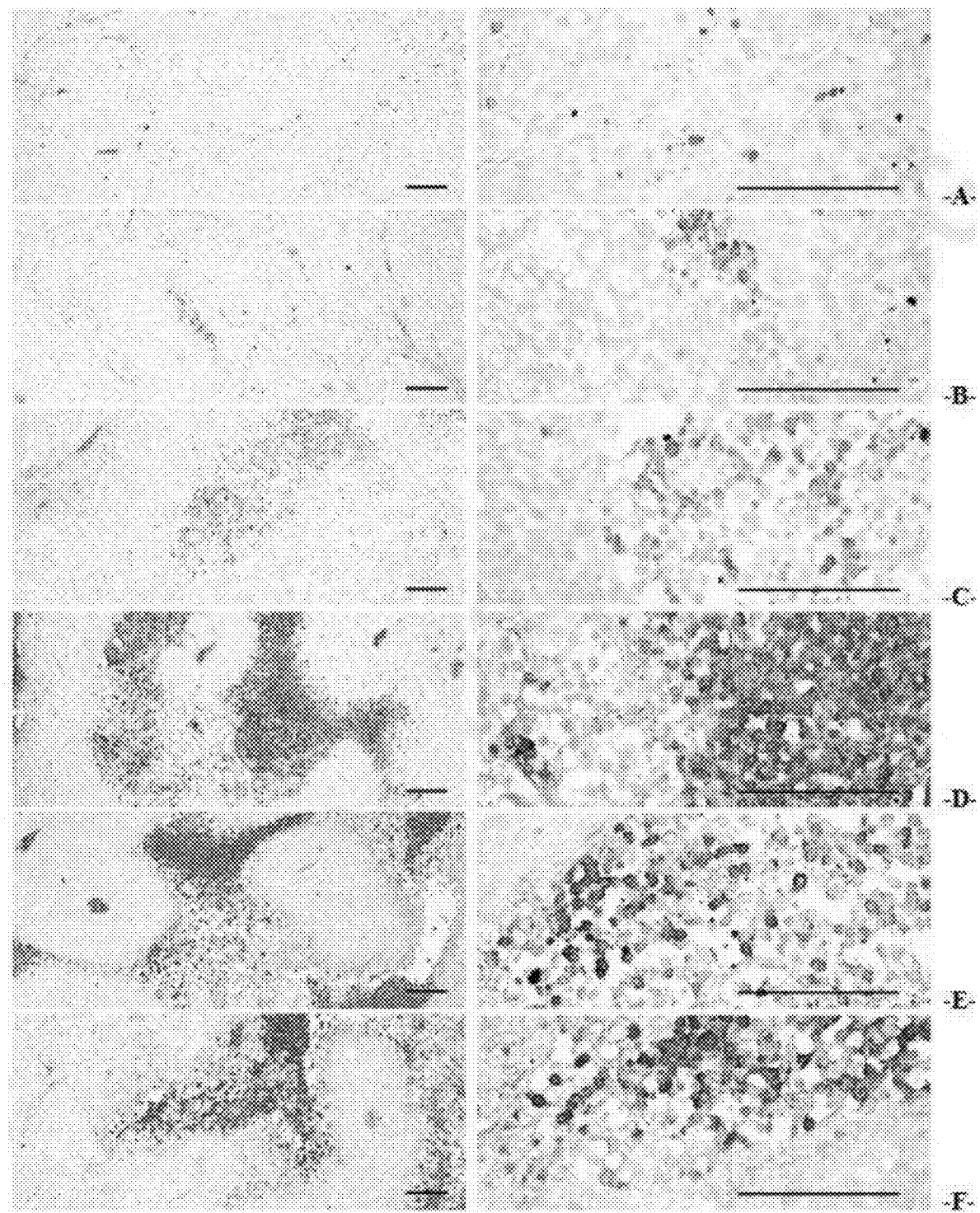

All the administered groups including the SKOG 400 mg/kg single administered group showed significant increases in intratumoral caspase-3 and PARP immune response cells compared with the tumor xenograft control group (p<0.01). Especially, the GSK 400, 200, and 100 mg/kg administered groups showed significant increases in the numbers of caspase-3 and PARP immune response cells compared with the gefitinib single administered group (p<0.01 or p<0.05) (Table 10 and FIGS. 11 and 12). The SKOG 400 mg/kg single group or the GSK 400, 200, and 100 mg/kg administered groups showed significant increase in the numbers of intratumoral iNOS and TNF-α immune response cells and a significant reduction in the number of COX-2 immune response cells compared with the tumor xenograft control group (p<0.01). Especially, the GSK 400, 200, and 100 mg/kg administered groups showed significant increases in the numbers of iNOS and TNF-α immune response cells (p<0.01) and a significant reduction in the number of COX-2 immune response cells (p<0.05) compared with the gefitinib single administered group. The gefitinib 120 mg/kg single composition administered group showed a significant reduction in the number of COX-2 immune response cells (p<0.01) but showed no significant changes in the numbers of iNOS and TNF-α immune response cells compared with the tumor xenograft control group (Table 10 and FIGS. 13 to 15).

As for the proportion of tumor cells in the tumor tissue, the gefitinib 120 mg/kg and SKOG 400 mg/kg single administered groups and the GSK 400, 200, and 100 mg/kg administered groups showed changes of −29.01, −16.44, −63.26, −51.32, and −42.29% compared with the tumor xenograft control group, respectively.

As for the proportion of apoptotic cells in the tumor tissue, the gefitinib 120 mg/kg and SKOG 400 mg/kg single administered groups and the GSK 400, 200, and 100 mg/kg administered groups showed changes of 560.23, 307.89, 1046.61, 895.25, and 765.22% compared with the tumor xenograft control group, respectively.

As for the proportion of caspase-3 immune response cells in the tumor tissue, the gefitinib 120 mg/kg and SKOG 400 mg/kg single administered groups and the GSK 400, 200, and 100 mg/kg administered groups showed changes of 268.77, 161.29, 585.11, 514.17, and 415.79% compared with the tumor xenograft control group, respectively.

As for the proportion of PARP immune response cells in the tumor tissue, the gefitinib 120 mg/kg and SKOG 400 mg/kg single administered groups and the GSK 400, 200, and 100 mg/kg administered groups showed changes of 223.59, 146.88, 494.32, 406.88, and 333.67% compared with the tumor xenograft control group, respectively.

As for the proportion of COX-2 immune response cells in the tumor tissue, the gefitinib 120 mg/kg and SKOG 400 mg/kg single administered groups and the GSK 400, 200, and 100 mg/kg administered groups showed changes of −35.00, −34.80, −80.15, −65.41, and −51.92% compared with the tumor xenograft control group, respectively.

As for the proportion of iNOS immune response cells in the tumor tissue, the gefitinib 120 mg/kg and SKOG 400 mg/kg single administered groups and the GSK 400, 200, and 100 mg/kg administered groups showed changes of −0.50, 206.23, 510.97, 425.71, and 243.25% compared with the tumor xenograft control group, respectively.

As for the proportion of TNF-α immune response cells in the tumor tissue, the gefitinib 120 mg/kg and SKOG 400 mg/kg single administered groups and the GSK 400, 200, and 100 mg/kg administered groups showed changes of −6.19, 377.65, 702.00, 602.72, and 441.11% compared with the tumor xenograft control group, respectively.

(2) Histopathological Change of Spleen

Figure 16:
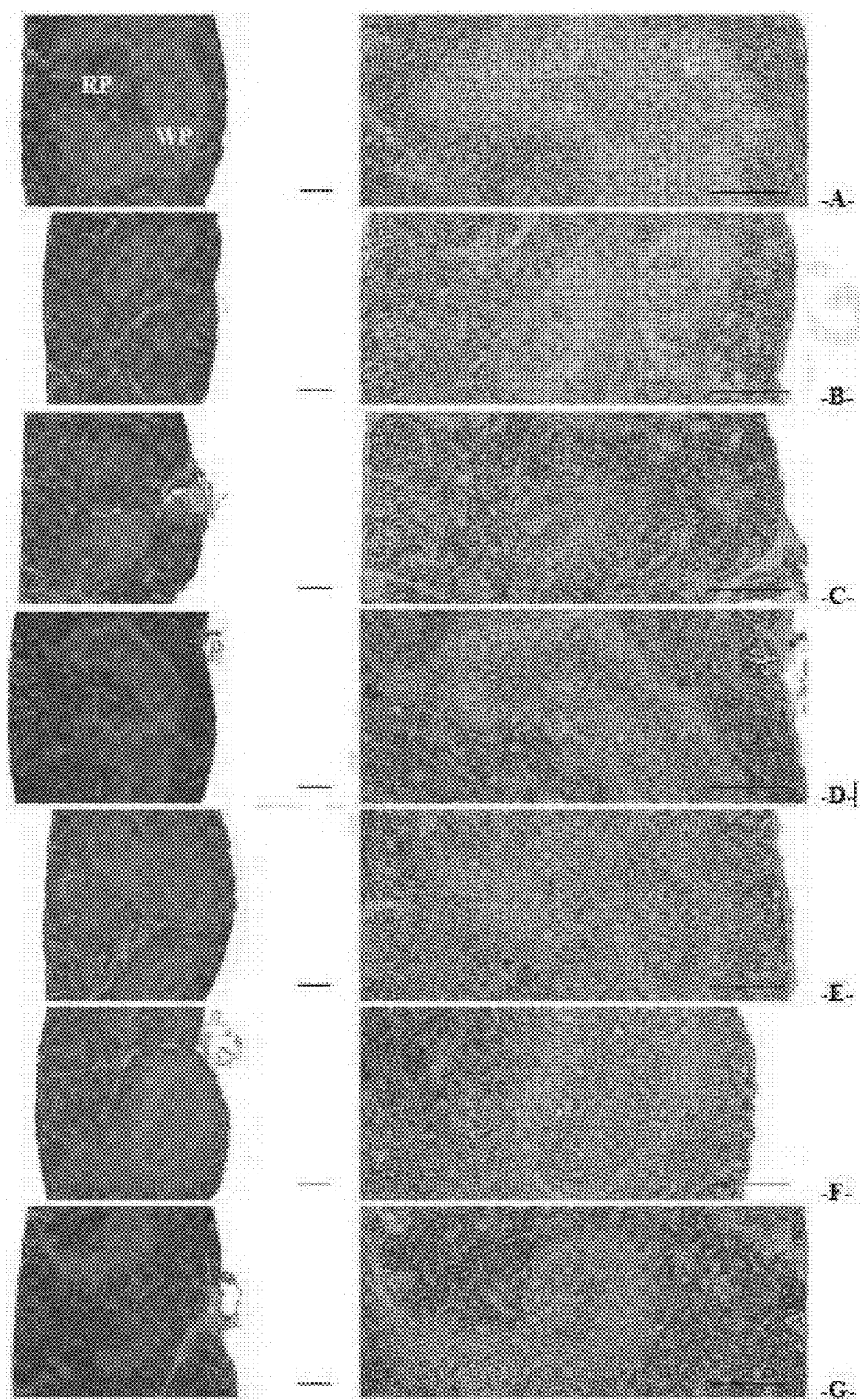
FIG. 16 shows changes of splenic red pulp (RP), white pulp (WP), and secondary follicles (G) in tumor cell xenograft mice according to SKOG or gefitinib single administration and SKOG and gefitinib co-administration.

The tumor xenograft control group showed atrophy characterized by a remarkable reduction in lymphocytes in the splenic white pulp portion compared with the normal medium control group, resulting in significant reductions in splenic thickness, white pulp diameter, and the number of white pulps ($p<0.01$). It was histopathologically confirmed that the SKOG 400 mg/kg single administered group and the GSK 400, 200, and 100 mg/kg administered groups showed significant increases in splenic thickness, white pulp diameter, and the number of white pulps compared with the tumor xenograft control group ($p<0.01$), and especially the SKOG 400 mg/kg single group and the GSK 400, 200, and 100 mg/kg administered groups showed significant increases in splenic thickness, white pulp diameter, and the number of white pulps compared with the gefitinib single administered group ($p<0.01$). The gefitinib single administered group showed similar changes in splenic thickness, white pulp diameter, and the number of white pulps compared with the tumor xenograft control group (Table 11 and FIG. 16).

TABLE 11

| Group | Splenic overall thickness (mm/central region) | Number of splenic white pulps (/mm²) | Splenic white pulp diameter (μm/white pulp) |
|---|---|---|---|
| Conrol group | | | |
| Intact | 1749.75 ± 190.38 | 14.75 ± 2.92 | 645.75 ± 127.16 |
| TB | 989.25 ± 135.20$^a$ | 4.88 ± 1.13$^a$ | 188.75 ± 69.98$^e$ |
| Single material administered group | | | |
| Gefitinib | 993.38 ± 131.85$^a$ | 4.63 ± 1.85$^a$ | 187.63 ± 73.54$^e$ |
| SKOG | 1281.50 ± 123.37$^{acd}$ | 8.25 ± 1.67$^{acd}$ | 323.00 ± 66.08$^{efg}$ |
| Gefitinib and SKOG co-administered group (wtihin 5 min) | | | |
| 400 mg/kg | 1489.75 ± 136.36$^{acd}$ | 13.88 ± 2.64$^{cd}$ | 449.50 ± 38.91$^{efg}$ |
| 200 mg/kg | 1340.38 ± 77940$^{acd}$ | 12.75 ± 1.28$^{bcd}$ | 404.75 ± 50.76$^{efg}$ |
| 100 mg/kg | 1276.13 ± 201.59$^{acd}$ | 8.63 ± 1.30$^{acd}$ | 352.50 ± 75.45$^{efg}$ |

As for the splenic overall thickness, the tumor xenograft control group showed a change of −43.46% compared with the normal medium control group, and the gefitinib 120 mg/kg and SKOG 400 mg/kg single administered groups and the GSK 400, 200, and 100 mg/kg administered groups showed changes of 0.42, 29.54, 50.59, 35.49, and 29.00% compared with the tumor xenograft control group, respectively.

As for the number of splenic white pulps, the tumor xenograft control group showed a change of −66.95% compared with the normal medium control group, and the gefitinib 120 mg/kg and SKOG 400 mg/kg single administered groups and the GSK 400, 200, and 100 mg/kg administered groups showed changes of −5.13, 69.23, 184.62, 161.54, and 76.92% compared with the tumor xenograft control group, respectively.

As for the splenic white pulp diameter, the tumor xenograft control group showed a change of −70.77% compared with the normal medium control group, and the gefitinib 120 mg/kg and SKOG 400 mg/kg single administered groups and the GSK 400, 200, and 100 mg/kg administered groups showed changes of −0.60, 71.13, 138.15, 114.44, and 86.75% compared with the tumor xenograft control group, respectively.

(3) Histopathological Change of Submandibular Lymph Nodes

Figure 17:
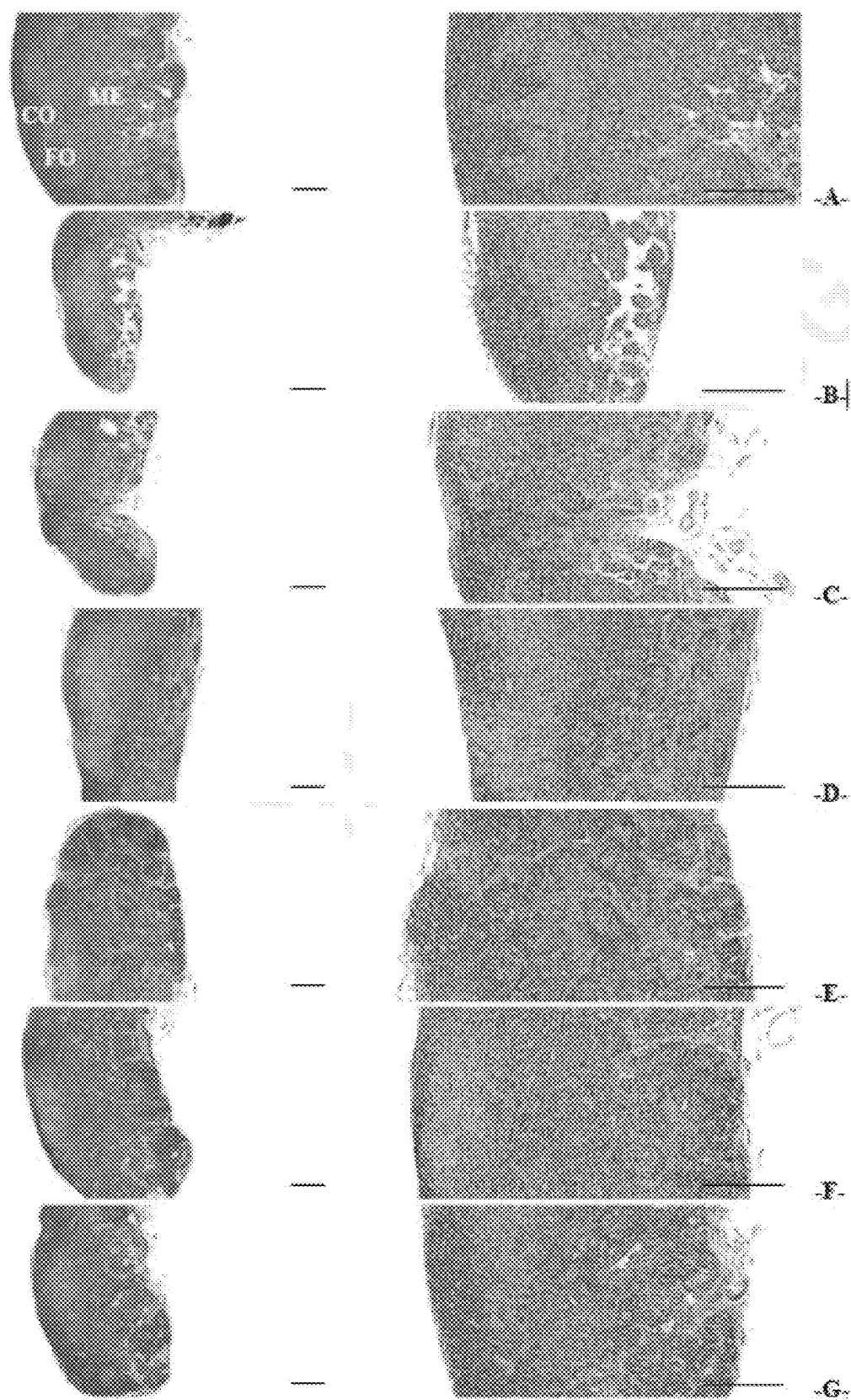

The tumor xenograft control group showed atrophy due to a remarkable reduction in lymphocytes in the lymph node cortex compared with the normal medium control group, resulting in significant reductions in submandibular lymph node overall and cortex thicknesses and number of intracortical follicles ($p<0.01$). However, the SKOG 400 mg/kg single administered group and the GSK 400, 200, and 100 mg/kg administered groups showed histopathologically significant increases in lymph node overall and cortex thicknesses and number of intracortical follicles compared with the tumor xenograft control group ($p<0.01$). Especially, the GSK 400, 200, and 100 mg/kg administered groups showed significant increases in lymph node overall and cortex thicknesses and number of intracortical follicles compared with the gefitinib single administered group ($p<0.01$). The gefitinib single administered group showed no significant changes in lymph node overall and cortex thicknesses and number of intracortical follicles compared with the tumor xenograft control group (Table 12 and FIG. 17).

TABLE 12

| Group | submandibular lymph node overall thickness (μm/central region) | Number of intracortical follicles (/mm²) | cortex thickness (μm/lymph node) |
|---|---|---|---|
| Control group | | | |
| Intact | 1127.63 ± 131.38 | 16.00 ± 3.93 | 540.50 ± 113.31 |
| TB | 514.63 ± 101.14$^a$ | 5.75 ± 1.28$^d$ | 224.38 ± 41.00$^d$ |
| Single material administered group | | | |
| Gefitinib | 501.50 ± 106.64$^a$ | 5.38 ± 2.39$^d$ | 215.75 ± 43.93$^d$ |
| SKOG | 744.00 ± 111.81$^{abc}$ | 8.63 ± 1.30$^{d/g}$ | 306.88 ± 25.76$^{d/g}$ |
| Gefitinib and SKOG co-administered group (wtihin 5 min) | | | |
| 400 mg/kg | 843.50 ± 113.09$^{abc}$ | 13.00 ± 2.73$^g$ | 423.25 ± 46.48$^{e/g}$ |
| 200 mg/kg | 868.63 ± 113.53$^{abc}$ | 10.50 ± 1.93$^{d/g}$ | 380.75 ± 43.65$^{d/g}$ |
| 100 mg/kg | 727.51 ± 103.85$^{abc}$ | 8.88 ± 1.25$^{d/g}$ | 328.38 ± 49.75$^{d/g}$ |

As for the submandibular lymph node overall thickness, the tumor xenograft control group showed a change of −54.36% compared with the normal medium control group, and the 120 mg/kg and SKOG 400 mg/kg single administered groups and the GSK 400, 200, and 100 mg/kg administered groups showed changes of −2.55, 44.57, 63.91, 49.36, and 41.37%, respectively, compared with the tumor xenograft control group.

As for the number of intracortical follicles in the submandibular lymph nodes, the tumor xenograft control group showed a change of −64.06% compared with the normal medium control group, and the gefitinib 120 mg/kg and SKOG 400 mg/kg single administered groups and the GSK 400, 200, and 100 mg/kg administered groups showed changes of −6.52, 50.00, 126.09, 82.61, and 54.35%, respectively, compared with the tumor xenograft control group.

As for the submandibular lymph node cortex thickness, the tumor xenograft control group showed a change of −58.490 compared with the normal medium control group, and the 120 mg/kg and SKOG 400 mg/kg single administered groups and the GSK 400, 200, and 100 mg/kg administered groups showed changes of −3.84, 36.77, 88.64, 69.69, and 46.35%, respectively, compared with the tumor xenograft control group.

(4) Histopathological Change of Periovarian Fat

Figure 18:
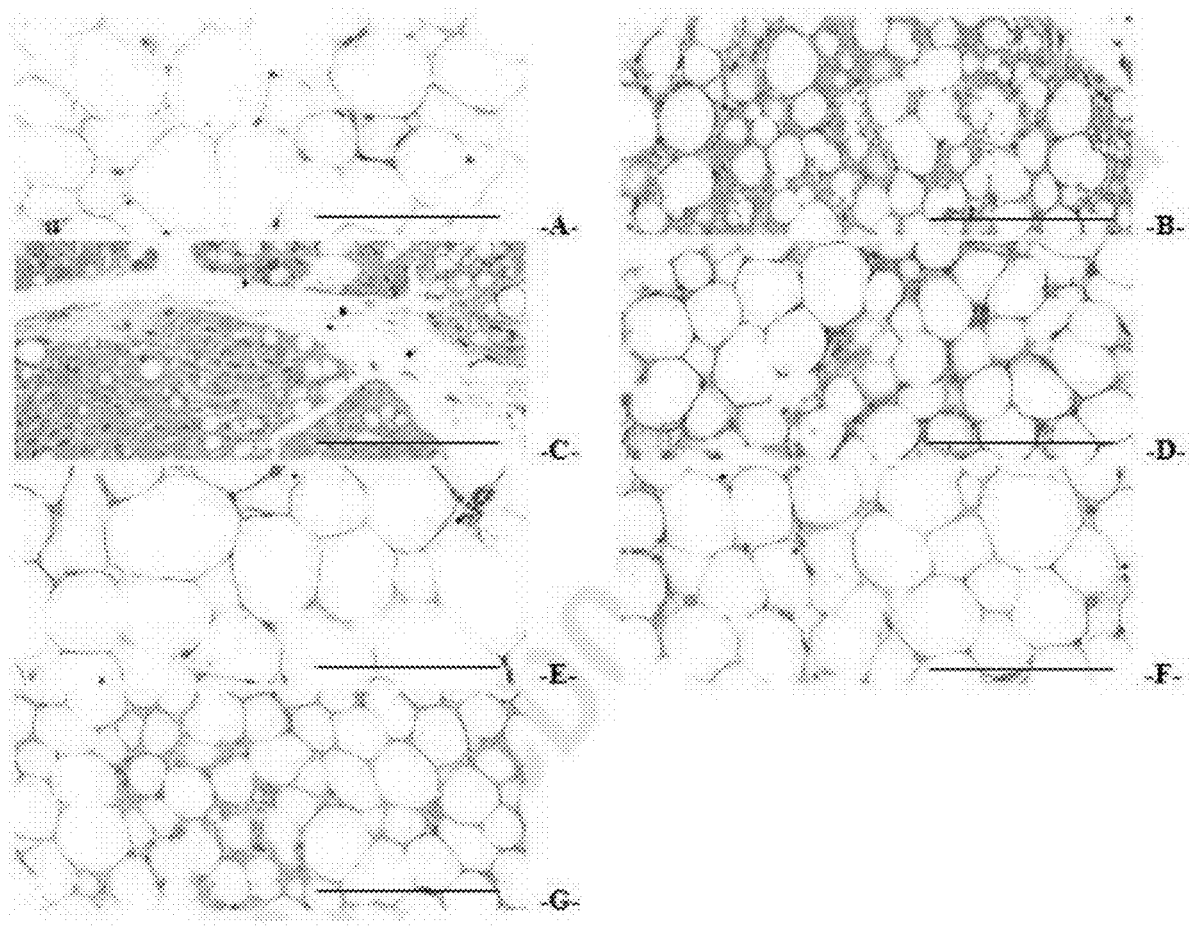

The tumor xenograft control group showed atrophy characterized by a remarkable reduction in white fat cell size compared with the normal medium control group, resulting in significant reductions in accumulation fat thickness and white fat cell average diameter (p<0.01). The SKOG 400 mg/kg single administered group and the GSK 400, 200, and 100 mg/kg administered groups showed histopathologically significant increases in accumulation fat thickness and white fat cell average diameter compared with the tumor xenograft control group, respectively (p<0.01), and especially, the GSK 400, 200, and 100 mg/kg administered groups showed significant increases in accumulation fat thickness and white fat cell average diameter compared with the gefitinib single administered group (p<0.01). The gefitinib single administered group showed similar changes in periovarian accumulation fat tissue thickness and white fat cell average diameter compared with the tumor xenograft control group (Table 13 and FIG. 18).

TABLE 13

| Group | Accumulation fat thickness (mm/central regions) | White fat cell average diameter (μm) |
|---|---|---|
| Control group | | |
| Intact | 1752.13 ± 201.31 | 52.11 ± 5.21 |
| TB | 409.25 ± 103.05$^a$ | 13.20 ± 2.61$^d$ |
| Single material administered group | | |
| Gefitinib | 375.75 ± 91.45$^a$ | 12.36 ± 1.95$^d$ |
| SKOG | 650.00 ± 121.29$^{abc}$ | 21.85 ± 3.14$^{def}$ |
| Gefitinib and SKOG co-administered group (within 5 min) | | |
| 400 mg/kg | 1453.00 ± 192.34$^{abc}$ | 37.95 ± 10.89$^{def}$ |
| 200 mg/kg | 1096.00 ± 128.90$^{abc}$ | 32.51 ± 11.42$^{def}$ |
| 100 mg/kg | 965.00 ± 192.82$^{abc}$ | 25.10 ± 6.62$^{def}$ |

As for the periovarian accumulation fat thickness, the tumor xenograft control group showed a change of −76.64% compared with the normal medium control group, and the gefitinib 120 mg/kg and SKOG 400 mg/kg single administered groups and the GSK 400, 200, and 100 mg/kg administered groups showed changes of −8.19, 58.83, 255.04, 167.81, and 135.80%, respectively, compared with the tumor xenograft control group.

As for the white fat cell average diameter, the tumor xenograft control group showed a change of −74.67% compared with the normal medium control group, and the gefitinib 120 mg/kg and SKOG 400 mg/kg single administered groups and the GSK 400, 200, and 100 mg/kg administered groups showed changes of −6.37, 68.51, 187.53, 146.30, and 90.11%, respectively, compared with the tumor xenograft control group.

The invention claimed is:

1. A method for treatment of cancer comprising a step:
   administering, to a subject, a composition comprising *Panax ginseng*, *Adenophorae triphylla*, *Wolfiporia extensa*, *Rehmannia glutinosa*, mel, and gefitinib.

2. The method of claim 1, wherein the composition comprises 4-5 wt % of *Panax ginseng*, 4-5 wt % of *Adenophorae triphylla*, 8-10 wt % of *Wolfiporia extensa*, 43-48 wt % of *Rehmannia glutinosa*, and 35-40 wt % of mel.

3. The method of claim 1, wherein the composition comprises 4-5 wt % of *Panax ginseng* dried powder, 4-5 wt % of *Adenophorae triphylla* dried powder, 8-10 wt % of *Wolfiporia extensa* dried powder, 43-48 wt % of *Rehmannia glutinosa* juice extract, and 35-40 wt % of mel.

* * * * *